United States Patent [19]

Magerlein

[11] 3,962,293

[45] June 8, 1976

[54] 13,14-DIHYDRO-16-FLUORO PROSTAGLANDIN $F_1$ ANALOGS

[75] Inventor: Barney J. Magerlein, Portage, Mich.

[73] Assignee: The Upjohn Company, Kalamazoo, Mich.

[22] Filed: Feb. 21, 1975

[21] Appl. No.: 551,694

Related U.S. Application Data

[60] Division of Ser. No. 381,155, July 20, 1973, which is a continuation-in-part of Ser. No. 248,013, April 27, 1972, abandoned.

[52] U.S. Cl. .............................. 260/408; 260/211 R; 260/247.2 R; 260/268 R; 260/293.65; 260/326.2; 260/429.9; 260/439 R; 260/448 R; 260/468 D; 260/488 R; 260/501.1; 260/501.15; 260/501.17; 260/501.2; 260/514 D

[51] Int. Cl.² .................. C07C 61/38; C07C 69/74

[58] Field of Search ........ 260/468 D, 514 D, 408 C, 260/408 F

[56] References Cited
OTHER PUBLICATIONS

Nakanishi et al., JACS 81 5259 (1959).

*Primary Examiner*—Robert Gerstl
*Attorney, Agent, or Firm*—Morris L. Nielsen; Robert A. Armitage

[57] ABSTRACT

Prostaglandin-type compounds with one or two fluoro substituents at the C-16 position are disclosed, with processes for making them. These compounds are useful for a variety of pharmacological purposes, including anti-ulcer, inhibition of platelet aggregation, increase of nasal patency, labor inducement at term, and wound healing.

19 Claims, No Drawings

13,14-DIHYDRO-16-FLUORO PROSTAGLANDIN F₁ ANALOGS

CROSS REFERENCE TO RELATED APPLICATIONS

This is a division of application Ser. No. 381,155, filed July 20, 1973 which is a continuation-in-part of my copending application Ser. No. 248,013 filed Apr. 27, 1972, now abandoned.

BACKGROUND OF THE INVENTION

This invention relates to novel compositions of matter, to novel methods for producing those, and to novel chemical intermediates useful in those processes. Particularly, this invention relates to certain novel analogs of some of the known prostaglandins in which there are one or two fluoro substituents at the C-16 position, i.e. on the carbon atom adjacent to the hydroxy-substituted carbon in the methyl-terminated chain.

The known prostaglandins include, for example, prostaglandin $E_2$ ($PGE_2$), prostaglandin $F_2$ alpha and beta ($PCF_{2\alpha}$ and $PGF_{2\beta}$), prostaglandin $A_2$ ($PGA_2$), prostaglandin $B_2$ ($PGB_2$), and the corresponding PGE compounds. Each of the above-mentioned known prostaglandins is a derivative o prostanoic acid which has the following structure and atom numbering:

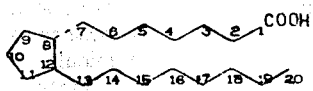

See, for example, Bergstrom et al., Pharmacol. Rev. 20, 1 (1968), and refeiences cited therein. A systematic name for prostanoic acid is 7-[(2β-octyl)-cyclopent-1α-yl]-heptanoic acid.

$PGE_2$ has the following structure:

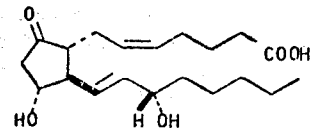

II $PGF_{2\alpha}$ has the following structure:

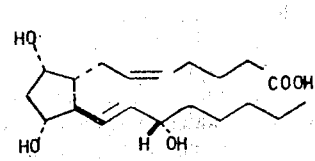

III $PGF_{2\beta}$ has the following structure:

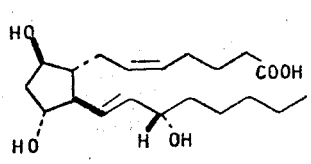

IV $PGA_2$ has the following structure:

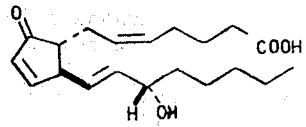

V $PGB_2$ has the following structure:

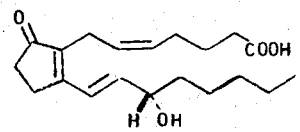

VI

Each of the known $PG_1$ prostaglandins, $PGE_1$, $PGE_{1\alpha}$, $PGF_{1\beta}$, $PGA_1$, and $PGB_1$, has a structure the same as that shown for the corresponding $PG_2$ compound except that, in each, the cis carbon-carbon double bond between C-5 and C-6 is replaced by a single bond. For example, $PGE_1$ has the following structure:

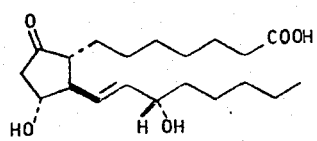

VII

In fomulas II to VII, as well as in the formulas given herinafter, broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring.

The side-chain hydroxy at C-15 in formulas II to VII is in S configuration. See Nature, 212, 38 (1966) for discussion of the stereochemistry of the prostaglandins.

Molecules of the known prostaglandins each have several centers of asymmetry, and can exist in racemic (optically inactive) form and in either of the two enantiomeric (optionally active) forms, i.e. the dextrorotatory and levorotatory forms. As drawn, formulas II to VII each represent the particular optically active form of the prostaglandin which is obtained from certain mammalian tissues, for example, sheep vesicular glands, swine lung, or human seminal plasma, or by carbonyl and/or double bond reduction of that prostaglandin. See, for example, Bergstrom et al., cited above. The mirror image of each of formulas II to VII represents the other enantiomer of that prostaglandin. The racemic form of a prostaglandin contains equal numbers of both enantiomeric molecules, and one of formulas II to VII and the mirror image of that formula is needed to represent correctly the corresponding racemic prostaglandin. For convenience hereinafter, use of the terms "$PGE_1$", "$PGE_2$", "$PGE_3$", "$PGF_{1\alpha}$", and the like, will mean the optically active form of that prostaglandin with the same absolute configuration as $PGE_1$ obtained from mammalian tissues. When reference to the racemic form of one of those psrostaglandins is intended, the word "racemic" or "dl" will preceed the prostaglandin name, thus, racemic $PGE_1$ or dl-$PGF_2\alpha$.

$PGE_1$, $PGE_2$, and the corresponding $PGF\alpha$, $PGF_\beta$, PGA, and PGB compounds, and their esters, acylates, and pharmacologically acceptable salts, are extremely potent in causing various biological responses. For that reason, these compounds are useful for pharmacological purposes. See, for example, Bergstrom et al., cited above. A few of those biological responses are systemic arterial blood pressure lowering in the case of the PGE, PGF$_\beta$, and PGA compounds as measured, for example, in anesthetized (pentobarbital sodium) pentolinium-treated rats with indwelling aortic and right heart cannulas; pressor activity, similarly measured, for the PGF$_\alpha$ compounds; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the central nervous system; controlling spasm and facilitating breathing in asthmatic conditions; decrease of blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE and PGB compounds, stimulation of epidermal proliferation and keratinization as shown when applied in culture to embryonic chick and rat skin segments.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

For example, these compounds, and especially the PGE compounds, are useful in mammals, including man, as nasal decongestants. For this purpose, the compounds are used in a dose range of about 10 $\mu$g. to about 10 mg. per ml. of a pharmacologically suitable liquid vehicle or as an aerosol spray, both for topical application, the exact dose depending upon the age, weight, and condition of the patient, and on the frequency and route of administration.

The PGE, PGF$_\alpha$, and PGA compounds are useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administation. For the above use these prostaglandins can be combined advantageously with other anti-asthmatic agents, such as sympathomimetics (isoproterenol, phenylephrine, ephedrine, etc); xanthine derivatives (theophylline and aminophyllin); and corticosteroids (ACTH and predinisolone). Regarding use of these compounds see South African Pat. No. 68/1055.

The PGE and PGA compounds are useful in mammals, including man and certain useful animals, e.g., dogs and pigs, to reduce and control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 $\mu$g. to about 500 $\mu$g. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

The PGE, PGF$_\alpha$, and PGF$_\beta$ compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and the treat conditions such as atherosclerosis, arteriosclerosis, blood clotting defects due to lipemia, and other clinical conditions in which the underlying etiology is associated with lipid imbalance or hyerlipidemia. For these purposes, these compounds are administered systemically, e.g., intravenously, subcutaneously, intramuscularly, and in the form of sterile implants for prolonged action. For rapid response, especially in emergency situation, the intravenous route of administration is preferred. Doses in the range about 0.005 to about 20 mg. per kg. of body weight per day are used, the exact dose depending on the age, weight, and condition of the patient or animal, and on the frequency and route of administration.

The PGE, PGF$_\alpha$, and PGF$_\beta$ compounds are especially useful as additives to blood, blood products, blood substitutes, and other fluids which are used in artifical extracorporeal circulation and perfusion of isolated body portions, e.g., limbs and organs, whether attached to the original body, detached and being preserved or prepared for transplant, or attached to the new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.0001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, PGE$_2$, for example, is useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50 μg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

The PGE, PGA, and PGFβ compounds are useful as hypotensive agents to reduce blood pressure in mammals, including man. For this purpose, the compounds are administered by intravenous infusion at the rate of about 0.01 to about 50 μg. per kg. of body weight per minute, or in single or multiple doses of about 25 to 500 μg. per kg. of body weight total per day.

The PGE, PGFα, and PGFβ compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 μg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

The PGE, PGFα, and PGFβ compounds are useful for controlling the reproductive cycle in ovulating female mammals, including humans and animals such as monkeys, rats, rabbits, dogs, cattle, and the like. By the term ovulating female mammals is meant animals which are mature enough to ovulate but not so old that regular ovulation has ceased. For that purpose, $PGF_{2\alpha}$, for example, is administered systemically at a dose level in the range of 0.01 mg. to about 20 mg. per kg. of body weight of the female mammal, advantageously during a span of time starting approximately at the time of ovulation and ending approximately at the time of menses or just prior to menses. Intravaginal and intrauterine are alternative routes of administration. Additionally, expulsion of an embryo or a fetus is accomplished by similar administration of the compound during the first third of the normal mammalian gestation period.

The PGE and PGF compounds are useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by PGE and PGF compounds is useful in assisting sperm movement to the uterus. Cervical dilation by prostaglandins is also useful in operative gynecology such as D and C (Cervical Dilation and Uterine Curettage) where mechanical dilation may case perforation of the uterus, cervical tears, or infections. It is also useful in diagnostic procedures where dilation is necessary for tissue examination. For these purposes, the PGE and PGF compounds are administered locally or systemically.

$PGE_2$, for example, is administered orally or vaginally at doses of about 5 to 50 mg. per treatment of an adult female human, with from one to five treatments per 24 hour period. $PGE_2$ is also administered intramuscularly or subcutaneously at doses of about one to 25 mg. per treatment. The exact dosages for these purposes depend on the age, weight, and condition of the patient or animal.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The PGA compounds and derivatives and salts thereof increase the flow of blood in the mammalian kidney, thereby increasing volume and electrolyte content of the urine. For that reason, PGA compounds are useful in managing cases of renal dysfunction, especially in cases of severely impaired renal blood flow, for example, the hepatorenal syndrome and early kidney transplant rejection. In cases of excessive or inappropriate ADH (antidiuretic hormone; vasopressin) secretion, the diuretic effect of these compounds is even greater. In anephretic states, the vasopressin action of these compounds is especially useful. Illustratively, the PGA compounds are useful to alleviate and correct cases of edema resulting, for example, from massive surface burns, and in the management of shock. For these purposes, the PGA compounds are preferably first administered by intravenous injection at a dose in the range 10 to 1000 μg. per kg. of body weight or by intravenous infusion at a dose in the range 0.1 to 20 μg. per kg. of body weight per minute until the desired effect is obtained. Subsequent doses are given by intravenous, intramuscular, or subcutaneous injection or infusion in the range 0.05 to 2 mg. per kg. of body weight per day.

The PGE and PGB compounds promote and accelerate the growth of epidermal cells and keratin in animals, including humans, useful domestic animals, pets, zoological specimens, and laboratory animals. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection or homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example intravenous injection or infusion, separate or in combination with the usual infusions of blood, plasma, or substitutes thereof. Alternative routes of administration are subcutaneous or intramuscular near the site, oral, sublingual buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 1 to 500 μg./ml. of the PGB compound or several times that concentration of the PGE compound. Especially for topical use, these prostaglandins are useful in combination with antibiotics, for example, gentamycin, neomycin, polymyxin B, bacitracin, spectinomycin, and oxytetracyline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of these being used in the combination at the usual concentration suitable for its use alone.

SUMMARY OF THE INVENTION

It is a purpose of this invention to provide novel 16-fluoro and 16,16-difluoro prostaglandin analogs in which there is variable chain length in the side chains. It is a further purpose to provide esters, lower alkanoates, and pharmacologically aceptable salts of said analogs. It is a further purpose to provide novel processes for preparing said analogs and esters. It is still a further purpose to provide novel intermediates useful in said processes.

The presently described acids and esters of the 16-fluoro and 16,16-difluoro prostaglandin analogs include compounds of the following formulas, and also the racemic compounds of each respective formula and the mirror image thereof

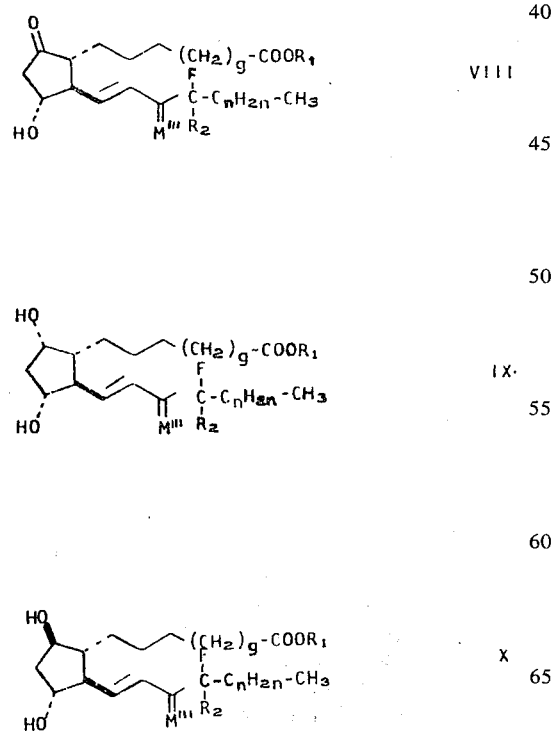

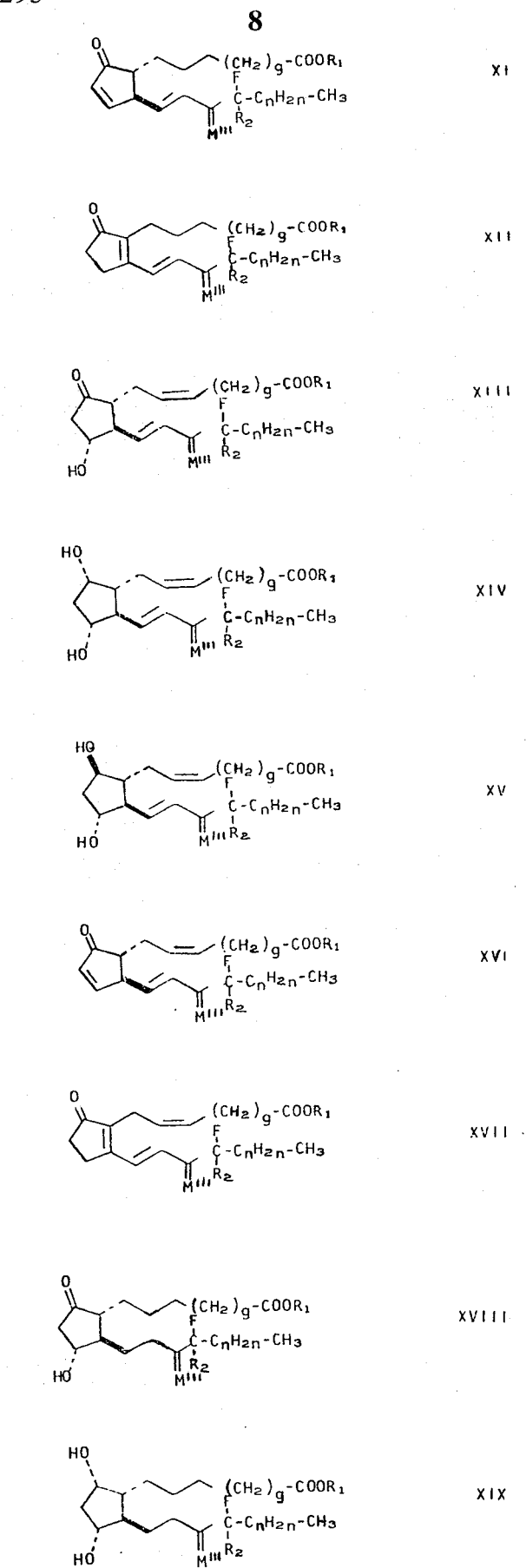

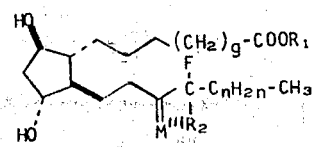 XX

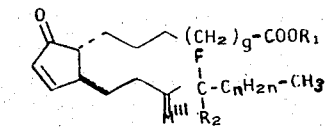 XXI

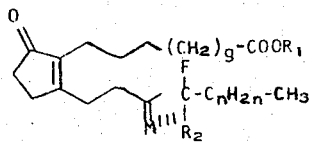 XXII

In formulas VIII to XXII, $C_nH_{2n}$ is alkylene of one to 9 carbon atoms, inclusive, with one to 6 carbon atoms, inclusive, in the chain between —$CFR_2$— and terminal methyl; g is an integer from 2 to 5, inclusive M''' is

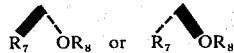

wherein $R_7$ and $R_8$ are hydrogen or alkyl of one to 4 carbon atoms, inclusive, being the same or different; $R_1$ is hydrogen or alkyl of one to 12 carbon atoms, inclusive; cycloalkyl of 3 to 10 carbon atoms, inclusive phenyl, or aralkyl of 7 to 12 carbon atoms, inclusive phenyl, or phenyl substituted with one, 2, or 3 chloro or alkyl of one to 4 carbon atoms, inclusive; and $R_2$ is hydrogen, methyl, ethyl or fluoro.

Formula IX represents 16($\alpha$ or $\beta$)-16-fluoro-19,20-dinor-PGF$_1\alpha$ when $C_nH_{2n}$ is methylene, g is 3, M''' is

and $R_1$ and $R_2$ are hydrogen. Formula XIII represents 16,16-difluoro-2$\alpha$,2$\beta$-dihomo-PGE$_2$ methyl ester when $C_nH_{2n}$ is $(CH_2)_3$, g is 5, M''' is

$R_1$ is methyl, and $R_2$ is fluoro. Formula XX represents 16-fluoro-16-methyl-20-methyl-2-nor-15$\beta$-13,14-dihydro-PGF$_1\beta$ when $C_nH_{2n}$ is $(CH_2)_4$, g is 2, M''' is

$R_1$ is hydrogen, and $R_2$ is methyl.

In the name of the formula-IX example above, "19,20-dinor" indicates absence of two carbon atoms from the hydroxy-substituted side chain of the PGF$_1\alpha$ structure. Following the atom numbering of the prostanoic acid structure, C-19 and C-20 are construed as missing, and the methylene at C-18 is replaced with a terminal methyl group. Likewise, in the formula-XX example, "2-nor" indicates the absence of the C-2 carbon atom from the carboxy terminated side chain. In this system of nomenclature, the words "nor", "dinor", "trinor", or "tetranor" in the names of the prostaglandin analogs are to be construed as indicating one, two, three, or four carbon atoms, respectively, missing from the C-2 to C-4 and C-18 to C-20 positions of the prostanoic acid carbon skeleton.

Following the conventional numbering of the carbon atoms in the prostanoic acid structure, C-16 designates the carbon atom adjacent to the hydroxy-substituted carbon atom (C-15).

In the name of the formula-XIII example, "2$\alpha$,2$\beta$-dihomo indicates two additional carbon atoms in the carboxy-terminated side chain specifically between the C-2 and C-3 carbon atoms. There are, therefore, nine carbon atoms in that side chain instead of the normal seven in the prostanoic acid structure. From the end of the chain to the double bond of the example they are identified as C-1, C-2, C-2$\alpha$, C-2$\beta$,C-3, C-4, and C-5. The carbon atoms connected by the cis double bond are C-5 and C-6, and the carbon atoms between the double bond and the ring are C-6 and C-7.

As in the case of formulas II to VII, formulas VIII to XXII, wherein M''' is

are each intended to represent optically active prostanoic acid derivatives with the same absolute configuration as PGE$_1$ obtained from mammalian tissues. For example, Formulas VIII to XXII wherein M''' is

represent compounds wherein the hydroxyl is attached to the side chain in alpha configuration. "15$\alpha$" refers to the same configuration as the absolute configuration of PGE$_1$ at C-15 obtained from mammalian tissues. When the name of a prostaglandin type compound herein does not include a designation of a stereochemistry at C-15, the compound referred to by such name is of the 15$\alpha$ configuration.

Also included within this invention are the 15-epimer compounds of formula VIII to XXII wherein M''' is

and the C-15 hydroxy is in beta configuration. Hereinafter "15$\beta$" refers to the epimeric configuration. Thus, "16-fluoro-19,20-dinor-15$\beta$-PGF$_1\alpha$" identifies the 15-epimeric compound corresponding to the formula-IX example above except that it has the beta configuration at C-15 instead of the natural alpha configuration of 16-fluoro-19,20-dinor-PGF$_1\alpha$ . Each of the formulas VIII to XXII plus its mirror image describe a racemic compound within the scope of this invention. For convenience hereinafter, such a racemic compound is designated by the prefix "racemic" (or "dl") before its name; when that prefix is absent, the intent is to designate an optically active compound represented by the appropriate formula VIII to XXII.

In formulas VIII to XXII, when R$_7$ is alkyl, each formula represents a 15-alkyl prostaglandin analog, for example 15-methyl, 15-ethyl, 15-propyl or 15-propyl or 15-butyl, including the isomers of propyl or butyl. For example formula XIV represents 15-methyl-16,16-difluoro-PGF$_2\alpha$ when g is 3, C$_n$H$_{2n}$ is trimethylene, R$_1$ is hydrogen, R$_2$ is fluoro, R$_7$ is methyl, and R$_8$ is hydrogen, i.e. M''' is

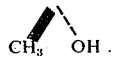

Further, in formulas VIII to XXII, when R$_8$ is alkyl, each formula represents a 15-alkyl ether. For example, formula XIV represents 16,16-difluoro-PGF$_2\alpha$, 15-methyl ether, when g is 3, C$_n$H$_{2n}$ is trimethylene R$_1$ is hydrogen, R$_2$ is fluoro, R$_7$ is hydrogen and R$_8$ is methyl, i.e., M''' is

With regard to formulas VIII to XXII, examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof. Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl, Examples of aralkyl of 7 to 12 carbon atoms, inclusive, are benzyl, phenethyl, 1-phenylethyl, 2-phenylpropyl, 4-phenylbutyl, 3-phenylbutyl, 2-(1-naphthylethyl), and 1-(2-naphthylmethyl). Examples of phenyl substituted by one to 3 chloro or alkyl of one to 4 carbon atoms, inclusive, are p-chlorophenyl, m-chlorophenyl, o-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of alkylene within the scope of —C$_n$H$_{2n}$— as defined above are methylene, ethylene, trimethylene, tetramethylene, pentamethylene, hexamethylene, and those alkylene with one or more alkyl substituents on one or more carbon atoms thereof, e.g. —CH(CH$_3$)—, —C(CH$_3$)$_2$—, —CH(CH$_2$CH$_3$)—, —CH$_2$—CH(CH$_3$)—, —CH(CH$_3$)—CH(CH$_3$)—, —CH$_3$—C(CH$_3$)$_2$—, —CH$_2$—CH(CH$_3$)—CH$_2$—, —CH$_2$—CH$_2$—CH(CH$_2$CH$_2$CH$_2$)—, and the like.

Accordingly, there is provided an optically active compound of the formula

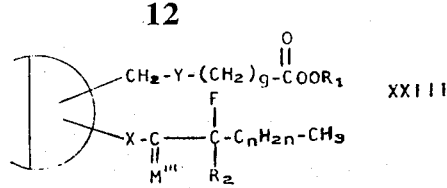

or a racemic compound of that formula and the mirror image thereof, wherein ⟩ is one of the four carbocyclic moieties:

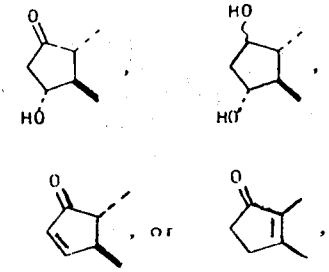

wherein ~ indicates attachment of hydroxyl to the ring in alpha or beta configuration: wherein (a) X is trans—CH=CH— or —CH$_2$CH$_2$—, and Y is —CH$_2$CH$_2$—, or (b) X is trans CH=CH— and Y is cis—CH=CH—; wherein C$_n$H$_{2n}$ is alkylene of one to 9 carbon atoms, inclusive, wth one to 6 carbom atoms, inclusive, in the chain between —CPR$_2$— and terminal methyl: wherein g is an integer from 2 to 5, inclusive: wherein M''' is

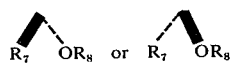

wherein R$_7$ and R$_8$ are hydrogen or alkyl of one to 4 carbon atoms, inclusive, being the same or different; wherein R$_1$ is hydrogen or alkyl of one to 12 carbon atoms, inclusive; cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; and wherein R$_2$ is hydrogen, methyl, ethyl, or fluoro; including the lower alkanoates thereof, and the pharmacologically acceptable salts thereof when R$_1$ is hydrogen.

Formula XXIII, which is written in generic form for convenience, represents PGE-type compounds when ⟩ is

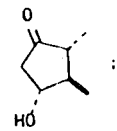

PGF$_\alpha$ -type compounds when ⟩ is

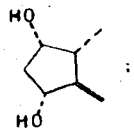

PGE$_\beta$ type compounds when ⟩ is

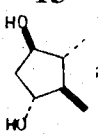

PGA-type compounds when ⟩ is

and PGB-type compounds when ⟩ is

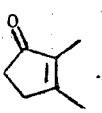

The novel formula VIII-to-XXIII compounds and the racemic compounds of this invention each cause the biological responses described above for the PGE, PGE$_\alpha$, PGE$_\beta$, PGA, and PGB compounds, respectively, and each of these novel compounds is accordingly useful for the abovedescribed corresponding purposes, and is used for those purposes in the same manner as described above.

The known PGE, PGF$_\alpha$, PGF$_\beta$, PGA, and PGB compounds are all potent in causing multiple biological responses even at low doses. For example, PGE$_1$ and PGE$_2$ both cause vasodepression and smooth muscle stimulation at the same time they exert antipolytic activity. Moreover, for many aplications, these known prostaglandins have an inconveniently short duration of biological activity. In striking contrast, the novel prostaglandin analogs of formulas VIII to XXIII and their racemic compounds are subsantially more specific with regard to potency in causing prostaglandin-like biological responses, and have a substantially longer duration of biological activity. Therefore, each of these novel prostaglandin analogs is surprisingly and unexpectedly more useful than one of the corresponding above-mentioned known prostaglandins for at least one of the pharmacological purposes indicated above for the latter, because it has a different and narrower spectrum of biological potency than the known prostaglandin, and therefore is more specific in its activity and causes smaller and fewer undesired side effects than when the known prostaglandin is used for the same purpose. Moreover, because of its prolonged activity, fewer and smaller doses of the novel prostaglandin analog can frequently be used to attain the desired result.

To obtain the optimum combination of biological response specificity, potency, and duration of activity, certain compounds within the scope of formulas VIII to XXIII are preferred. For example, it is prefered that the hydroxyl at C-15 be in the alpha configuration.

Another preference is that any branching of the $C_nH_{2n}$ group in the hydroxy-substituted chain be at C-17. In the general expression $-C_nH_{2n}-CH_3$ as used herein, examples of such branching are $-CH(CH_3)-CH_3$, $-CH(CH_3)-CH_2H_3$, $-CH_2-CH(CH_3)-CH_3$, $-C(CH_3)_2-CH_2-CH_3$, $-CH(CH_3)-CH(CH_2)-CH_3$, $-C(CH_3)_2-C(CH_3)_2-CH_2-CH_3$, $-CH(CH_3)-(CH_2)_2-CH_3$, and $-C(CH_3)_2-(CH_2)_5-CH_3$. Especially preferred are those wherein the $-C_nH_{2n}-CH_3$ chain length is 3 to 5 carbon atoms.

Another preference is that g be 3 when $C_nH_{2n}$ has one, 2, 4, 5, or 6 carbon atoms in the chain between $-CFR_2-$ and terminal methyl. Still another preference is that $C_nH_{2n}$ have 3 carbon atoms in the chain between $-CRF_2-$ and terminal methyl when g is 2, 4, or 5.

Another advantage of the novel compounds of this invention, especially the preferred compounds defined hereinabove, compared with the known prostaglandins, is that these novel compounds are administered effectively orally, sublingually, intravaginally, buccally, or rectally, in addition to usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

The 16-fluoro and 16,16-difluoro PGE, PGF$_\alpha$, PGF$_\beta$, PGA, and PGB-type analogs encompassed by formulas VIII to XXIII including their alkanoates, are used for the purposes described above in the free acid form, in ester form, or in pharmacologically acceptable salt form. When the ester form is used, the ester is any of those within the above definition of $R_1$. However, it is preferred that the ester be alkyl of one to 12 carbon atoms, inclusive. Of those alkyl, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable salts of these formula VIII-to-XXIII compounds useful for the purposes described above are those with pharmacologically acceptable metal cations, ammonium, amine cations, or quaternary ammonium cations.

Especially preferred metal cations are those derived from the alkali metals, e.g., lithium, sodium and potassium, and from the alkaline earth metlas, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolodine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amyiphenyl)-diethanolamine, galactamine, N-methylglycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The compounds encompassed by formulas VIII to XXIII are used for the purposes described above in free hydroxy form or also in the form wherein the hydroxy moieties are transformed to lower alkanoate moieties, e.g., —OH to —OCOCH$_3$. Examples of lower alkanoate moieties are acetoxy, propionyloxy, butyryloxy, valeryloxy, hexanoyloxy, heptanoyloxy, octanoyloxy, and branched chain alkanoyloxy isomers of those moieties. Especially preferred among these alkanoates for the above described purposes are the acetoxy compounds. These free hydroxy and alkanoyloxy compounds are used as free acids, as esters, and in salt form all as described above.

As discussed above, the compounds of formulas VIII to XXIII are administered in various ways for various purposes: e.g., intravenously, intramuscularly, subcutaneously, orally, intravaginally, rectally, buccally, sublingually, topically, and in the form of sterile implants for prolonged action. For intravenous injection or infusion, sterile aqueous isotonic solutions are preferred. For that purpose, it is preferred because of increased water solubility that $R_1$ in the formula VIII-to-XXIII compound be hydrogen or a pharmacologically acceptable cation. For subcataneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral sublingual administration. For rectal or vaginal administration, suppositories prepared as known in the art are used. For tissue implants, a sterile tablet or silicone rubber capsule or other object containing or impregnated with the substance is used.

The 16-fluoro and 16,16-difluoro PGE-, PGFα -, PGFβ -, PGA-, and PGB-type analogs encompassed by formulas VIII to XXIII are produced by the reactions and procedures described and exemplified hereinafter.

Reference to Charts A and B herein, will make clear the steps for preparing the formula-XXIV through XXXIV intermediates.

Previously, the preparation of an intermediate bicyclic lactone diol of the formula

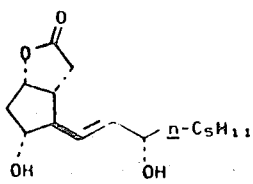

was reported by E. J. Corey et al., J. Am. Chem. Soc. 91, 5675 (1969), and later disclosed in an optically active form by E. J. Corey et al., J. Am. Chem. Soc. 92, 397 (1970). Conversion of this intermediate to PGE$_2$ and PGF$_{2\alpha}$, either in racemic or optically active form, was disclosed in those publications.

The iodolactone of formula XXIV in Chart A is known in the art (see Corey et al., above). It is available in either racemic or optically active (+ or −) form. For racemic products, the racemic form is used. For prostaglandins of natural configuration, the laevorotatory form (−) is used.

In Charts A and B, $C_nH_{2n}$, g, M, and $R_2$ have the same

CHART A

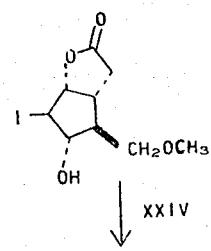

XXIV

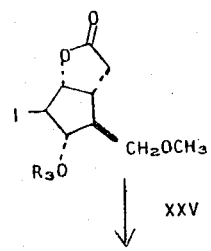

XXV

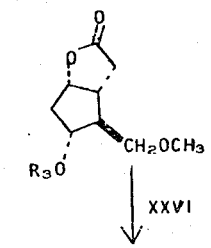

XXVI

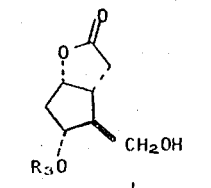

XXVII

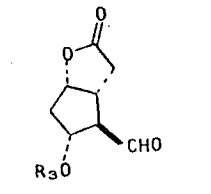

XXVIII

CHART B

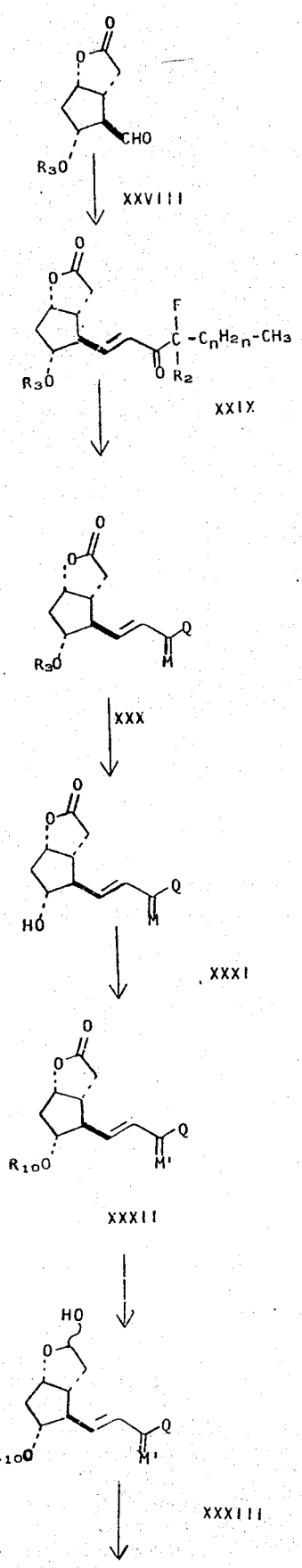

CHART B (continued)

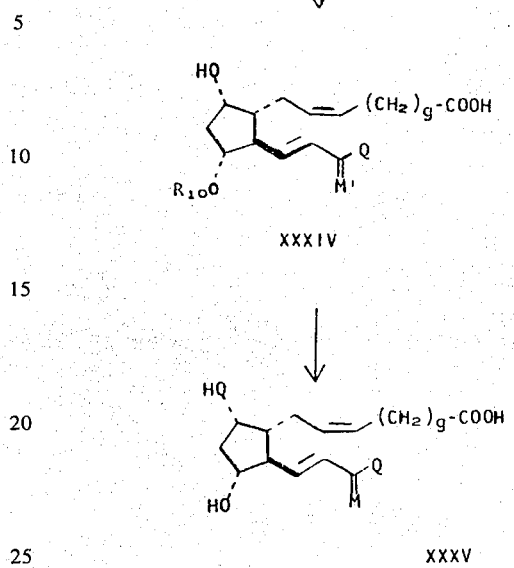

meanings as defined above, namely: $C_nH_{2n}$ is alkylene of one to 9 carbon atoms, inclusive, with one to 6 carbon atoms, inclusive, in the chain between $-CFR_2-$ and terminal methyl; g is an integer from 2 to 5, inclusive; M is

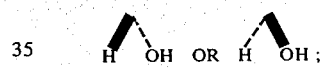

and $R_2$ is hydrogen, methyl, or ethyl, or fluoro.

In Chart B, M' is

wherein $R_{10}$ is a "blocking group", which is defined as any group which replaces hydrogen of the hydroxyl groups, which is not attacked by nor is reactive to the reagents used in the respective transformations to the extent that the hydroxyl group is, and which is subsequently replaceable by hydrogen at a later stage in the preparation of the porstaglandin-like products. Several blocking groups are known in the art, e.g. tetrahydropyranyl and substituted tetrahydropyranyl (see Corey, Proceedings of the Robert A. Welch Foundation Conferences on Chemical Research. XII, Organic Synthesis, pp. 51–79 (1969)). Thoe blocking groups which have been found useful include (a) tetrahydropyranyl; (b) tetrahydrofuranyl; or (c) a group of the formula

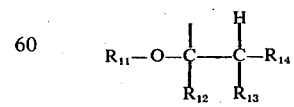

wherein $R_{11}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{12}$ and $R_{13}$ are the same or different, being hydrogen, alkyl of one to 4 carbon atoms, inclusive, phenyl or phenyl substituted with one, 2, or 3 alkyl of one to 4 carbon atoms, inclusive, or, when $R_{12}$ and $R_{13}$ are taken together, —(CH$_2$)a- or —(CH$_2$)b—O—(CH$_2$)c— wherein $a$ is 3, 4, or 5, $b$ is one, 2, or 3, and $c$ is one, 2, or 3 with the proviso that b plus c is 2, 3, or 4, and wherein R$_4$ is hydrogen or phenyl.

Further, in Chart B, Q is —CFR$_2$— C$_n$H$_{2n}$—CH$_3$ and ~ represents attachment of hydroxy in alpha or beta configuration. In Charts A and B, R$_3$ is (1) 

wherein T is alkyl of one to 4 carbon atoms, inclusive, phenylalkyl or 7 to 10 carbon atoms, inclusive, or nitro, and $s$ is zero to 5, inclusive, provided that not more than two T's are other than alkyl, and that the total number of carbon atoms in the T's does not exceed 10 carbon atoms;

(2) 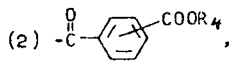

wherein R$_4$ is alkyl of one to 4 carbon atoms, inclusive;

(3) 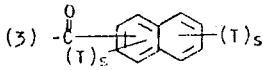

wherein T and $s$ are as defined above; or (4) acetyl. In preparing the formula-XXV compound by replacing the hydrogen of the hydroxyl group in the 4-position with the acyl group R$_3$, methods known in the art are used. Thus, an aromatic acid of the formula R$_3$OH, wherein R$_3$ is as defined above, for example benzoic acid, is reacted with the formula-XXIV compound in the presence of dehydrating agent, e.g. sulfuric acid, zinc chloride, or phosphoryl chloride; or an anhydride of the aromatic acid of the formula (R$_3$)$_2$O, for example benzoic anhydride, is used.

Preferably, however, an acyl halide, e.g. R$_3$Cl, for example benzoyl chloride, is reacted with the formula-XXIV compound in the presence of a hydrogen chloride-scavenger, e.g. a tertiary amine such as pyridine, triethylamine, and the like. The reaction is carried out under a variety of conditions using procedures generally known in the art. Generally, mild conditions are employed, e.g. 20–60° C., contacting the reactants in a liquid medium, e.g. excess pyridine or an inert solvent such as benzene, toluene or chloroform. The acylating agent is used either, in stoichiometric amount or in excess.

As examples of R$_3$, the following are available as acids (R$_3$OH), anhydrides ((R$_3$)$_2$O), or acyl chlorides (R$_3$Cl): benzoyl; substituted benzoyl, e.g. (2-, 3- or 4-)methylbenzoyl, (2-, 3-, or 4-)ethylbenzoyl, (2-, 3-, or 4-)isopropylbenzoyl, (2-, 3-, or 4-)tert-butylbenzoyl, 2,4-dimethylbenzoyl, 3,5-dimethylbenzoyl, 2-isopropyltoluyl, 2,4,6-trimethylbenzoyl, pentamethylbenzoyl, α-phenyl-(2-, 3-, or 4-)tolyl, (2-, 3-, or 4-)phenylbenzoyl, 2-, 3-, or 4-nitrobenzoyl, (2,4- 2,5- or 3,5-)dinitrobenzoyl, 3,4-dimethyl-2-nitrobenzoyl, 4,5-dimethyl-2-nitrobenzoyl. 2-nitro-6-phenethylbenz- oyl, 3-nitro-2-phenethylbenzoyl; mono-esterified phthaloyl, e.g.

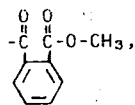

isophthaloyl, e.g.

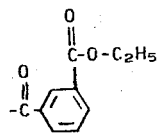

or terephthaloyl, e.g.

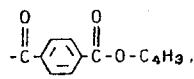

(1- or 2-)naphthoyl; substituted naphthoyl, e.g. (2-, 3-, 4-, 5-, 6-, or 7-)methyl-1-naphthoyl, (2- or 4-)ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, (3-,4-, 5-, or 8-)nitro-1-naphthoyl, 4,5-dinitro-1-naphthoyl, (3-, 4-, 6-, 7-, or 8-)methyl-1-naphthoyl, 4-ethyl-2-naphthoyl, and (5- or 8-)nitro-2-naphthoyl; and acetyl. There may be employed, therefore, benzoyl chloride, 4-nitrobenzoyl chloride, 3,5-dinitrobenzoyl chloride, and the like, i.e. R$_3$Cl compounds corresponding to the above R$_3$ groups. If the acyl chloride is not available, it is made from the corresponding acid and phosphorus pentachloride as is known in the art. It is preferred that the R$_3$OH, (R$_3$)$_2$O, or R$_3$Cl reactant does not have bulky, hindering substituents, e.g. tert-butyl, on both of the ring carbon atoms adjacent to the carbonyl attaching-site.

The formula-XXVI compound is next obtained by deiodination of XXV using a reagent which does not react with the lactone ring or the OR$_3$ moiety, e.g. zinc dust, sodium hydride, hydrazine-palladium, hydrogen and Raney nickel or platinum, and the like. Especially preferred is tributyltin hydride in benzene at about 25° C. with 2,2'-azobis(2-methylpropionitrile) as initiator.

The formula-XXVII compound is obtained by demethylation of XXVI with a reagent that does not attack the OR$_3$ moiety, for example boron tribromide or trichloride. The reaction is carried out preferably in an inert solvent at about 0–5° C.

The formula-XXVIII compound is obtained by oxidation of the —CH$_2$OH of XXVII to —CHO, avoiding decomposition of the lactone ring. Useful for this purpose are dichromatesulfuric acid, Jones reagent, lead tetraacetate, and the like. Especially preferred is Collins' reagent (pyridineCrO$_3$) at about 0°–10° C.

The formula-XXIX compound is obtained by Wittig alkylation of XXXI, using the sodio derivative of the appropriate 2-oxo-3-fluoro (or 3,3-difluoro)-alkylphosphonate. The trans enone lactone is obtained stereospecifically (see D.H. Wadsworth et al, J. Org. Chem. Vol. 30, p. 680 (1965)).

In preparing the formula-XXIX compounds of Chart B. certain phosphonates are employed in the Wittig reaction. These are of the general formula

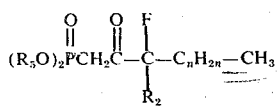

wherein $R_2$ is hydrogen, methyl, or ethyl, or fluoro, wherein $R_5$ is alkyl of one to 8 carbon atoms, inclusive, and $C_nH_{2n}$ is alkylene of one to 9 carbon atoms, inclusive, with one to 6 carbon atoms, inclusive, in the chain between —$CFR_2$— and terminal methyl. In preparing the preferred embodiments of this invention, phosphonates are used in which fluoro substitution is on the carbon atoms adjacent to the carbonyl, for example

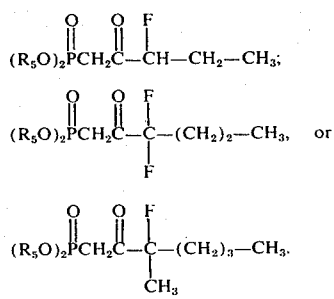

The phosphonates are prepared and used by methods known in the art. See Wadsworth et al., reference cited above. Conveniently, the appropriate aliphatic acid ester is condensed with dimethyl methylphosphonate in the presence of n-butyllithium. For this purpose, acids of the general formula $CH_3$—$C_nH_{2n}$—$CFR_2$—$COOH$ are used in the form of their lower alkyl esters, preferably methyl or ethyl. For this purpose methyl esters are readily formed from the acids by reaction with diazomethane. These aliphatic acids of various chain length, with mono- or difluoro substitution within the scope of —$CFR_2$— as defined above are known in the art or can be prepared by methods known in the art.

Many fluoro-substituted acids are readily available. e.g. 2-fluorobutyric, 2,2-difluorobutyric, 2-fluorovaleric, 2-fluorohexanoic, 2-fluoroheptanoic, 2-fluorooctanoic, 2-fluorononanoic, and 2-fluorodecanoic acids. Others are available by methods known in the art, for example by fluorination of 2-oxo aliphatic acids with sulfur tetrafluoride to give 2,2-difluoro acids. For reactions of $SF_4$ see Martin et al., J. Org. Chem. 27, 3164 (1962). For other syntheses of fluorinated acids see Henne et al., J. Am. Chem. Soc. 69, 281 (1947). For fluorination of a ketone function with $MoF_6BF_3$ see Mathey et al., Tetrahedron 27, 2965 (1971). Other methods of synthesis include replacement of hydroxy by fluoro, see Ayer, U.S. Pat. No. 3,056,806; replacement of chloro or bromo by exchange with fluorides, or saturation of double bonds by fluorine atoms, see Advances in Fluorine Chemistry, M. Stacey et al., editors, Vol. 3, Butterworth and Co., 1963, especially pages 181–188.

Continuing with Chart B, the formula-XXX compound is obtained as a mixture of alpha and beta isomers by reduction of XXIX. For this reduction, use is made of any of the known ketonic carbonyl reducing agents which do not reduce ester or acid groups or carbon-carbon double bonds when the latter is undesirable. Examples of those are the metal borohydrides, especially sodium, potassium, and zinc borohydrides, lithium (tri-tert-butoxy)aluminum hydride, metal trialkoxy borohydrides, e.g., sodium trimethoxyborohydride, lithium borohydride, diisobutyl aluminum hydride, and when carbon-carbon double bond reduction is not a problem, the boranes, e.g., disiamylborane (bis-3-methyl-2-butylborane).

For production of natural-configuration PG-type compounds, the desired 15-alpha form of the formula-XXX compound is separated from the 15-beta isomer by silica gel chromatography.

The formula-XXXI compound is then obtained by deacylation of XXX with an alkali metal carbonate, for example potassium carbonate in methanol at about 25° C.

When the blocking group $R_{10}$ is tetrahydropyranyl, the bis(tetrahydropyranyl ether) XXXII is obtained by reaction of the formula-XXXI diol with 2,3-dihydropyran in an inert solvent, e.g. dichloromethane, in the presence of an acid condensing agent such as p-toluenesulfonic acid or pyridine hydrochloride. The dihydropyran is used in excess, preferably 4 to 10 times theory. The reaction is normally complete in 15–30 min. at 20°–50° C. When the blocking group is tetrahydrofuranyl, 2,3-dihydrofuran is used, instead. When the blocking group is of the formula

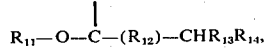

as defined above, the appropriate reagent is a vinyl ether, e.g. isobutyl vinyl ether or any vinyl ether of the formula

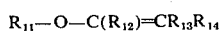

wherein $R_{11}$, $R_{12}$, $R_{13}$, and $R_{14}$ are as defined above; or an unsaturated cyclic or heterocyclic compound, e.g. 1-cyclohexen-1-yl methyl ether

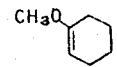

or 5,6-dihydro-4-methoxy-2H-pyran

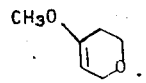

See C. B. Reese et al., J. Am. Chem. Soc. 89, 3366 (1967). The reaction conditions for such vinyl ethers and unsaturated compounds are similar to those for dihydropyran above.

The lactol XXXIII is obtained on reduction of the formula-XXXII lactone or its 15β epimer without reducing the 13,14-ethylenic group. For this purpose, diisobutyl-aluminum hydride is used. The reduction is preferably done at −60° to −70° C. The 15β-epimer of the formula-XXXII lactone is readily obtained by the steps of the Chart B, using the 15β isomer of formula XXX.

The formula-XXXIV compound is obtained from the formula-XXXIII lactol by the Wittig reaction, using a Wittig reagent derived from the appropriate ω-carboxyalkyltriphenylphosphonium bromide, HOO- C—$(CH_2)_{g+1}$—P(c $H_5)_3$Br, and sodio dimethylsulfinylcarbanide. The reaction is conveniently carried out at about 25° C. This formula-XXXIV compound serves as an intermediate for preparing either the $PGF_{2\alpha}$-type or the $PGE_2$-type product (Chart C). The phosphonium compounds are known in the art or are readily available, e.g. by reaction of an ω-bromoaliphatic acid with triphenylphosphine.

The formula-XXXV $PGF_{2\alpha}$-type product is obtained on hydrolysis of the blocking groups from the formula-XXXIV compound, e.g. with methanol—HCl, acetic acid/water/tetrahydrofuran, aqueous citric acid, or aqueous phosphoric acid-tetrahydrofuran, preferably at temperatures below 55° C., thereby avoiding formation of $PGA_2$-type compounds as by-products. Reference to Chart C will make clear the preparation of the $PGE_2$-type products. The 11,-15-diether of the $PGF_{2\alpha}$-type products represented by

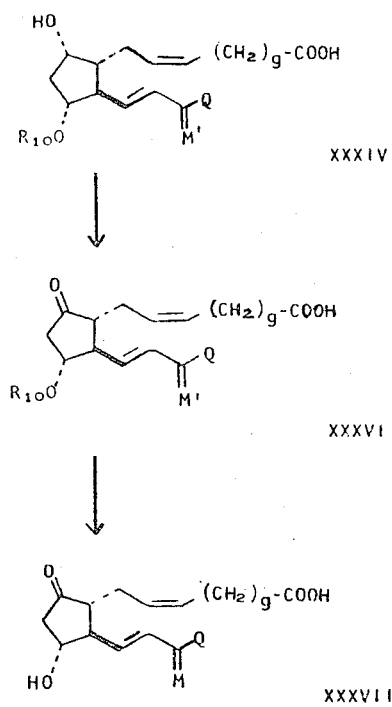

formula XXXIV is oxidized at the 9-hydroxy position, preferably with Jones reagent. Finally the blocking groups are replaced with hydrogen, by hydrolysis as in preparing the $PGF_{2\alpha}$-type product of Chart B. In Chart C, the symbols g, M, M′, Q, and $R_{10}$ have the same meanings as in Charts A and B.

Referring to Chart D, there is shown the transformation of lactone XXX to 15-alkyl ether PGF-type products of formula XLI. In Chart D, g, M, Q, $R_3$, $R_{10}$, and ~ have the same meanings as above. $M^v$ is either

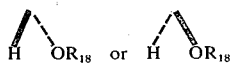

wherein $R_{18}$ is alkyl of one to 4 carbon atoms, inclusive. The starting materials are available from the steps of Chart B above or are readily available by methods known in the art.

The formula-XXXIX compound is prepared by alkylation of the side-chain hydroxy of the formula-XXX compound thereby replacing hydroxy with the —$OR_{18}$ moiety. For this purpose, diazoalkanes may be employed, preferably in the presence of a Lewis acid, e.g. boron trifluoride etherate. aluminum chloride, or fluoboric acid. When $R_{18}$ is methyl, diazomethane is used. See Fieser et al., "Reagents for Organic Synthesis", John Wiley and Sons, Inc., N.Y. (1967). p. 191. Other —$OR_{18}$ groups are formed by using the corresponding diazoalkane. For example diazoethane and diazobutene yield —$OC_2H_5$ and —$OC_4H_9$ respectively. The reaction is carried out by mixing a solution of the diazoalkane in a suitable inert solvent, preferably ethyl ether, with the formula-XXX compound. Generally, the reaction proceeds at about 25° C. Diazoalkanes are known in the art or can be prepared by methods known in the art. See,

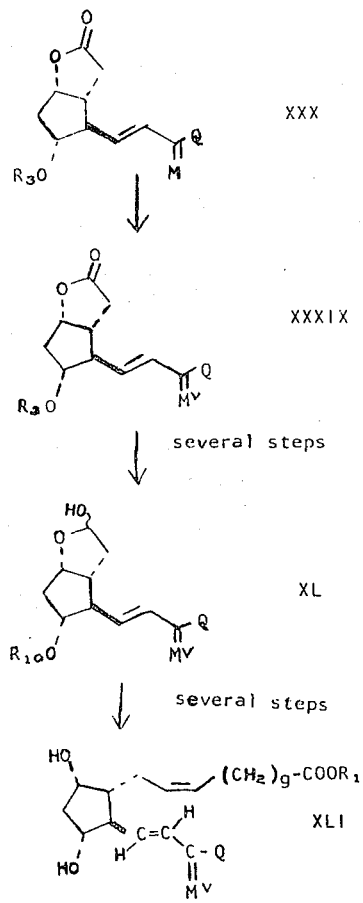

for example, Organic Reactions, John Wiley and Sons, Inc., N.Y. Vol. 8, pp. 389–394 (1954).

Another method for the alkylation of the side chain hydroxy is by reaction with an alcohol in the presence of boron trifluoride etherate. Thus, methanol and boron trifluoride etherate yield the methyl ether wherein $R_{18}$ is methyl. The reaction is done at about 25° C. and is conveniently followed with thin layer chromatography (TLC).

Another method for the alkylation of the side-chain hydroxy is by the reaction of an alkyl halide, e.g. methyl iodide, in the presence of a metal oxide or hydroxide, e.g. barium oxide, silver oxide, or barium hydroxide. An inert solvent may be beneficial, for example benzene or dimethylformamide. The reactants are preferably stirred together and maintained at temperatures of 25°–75° C.

Still another method is by first converting the hydroxy to mesyloxy (i.e. methanesulfonate) or tosyloxy (i.e. toluenesulfonate) and thence transforming the mesyloxy or tosyloxy to the —$OR_{18}$ moiety by reaction with a metal alkoxide, e.g. potassium tert-butoxide. The mesylate or tosylate is prepared by reaction of the formula-XXX intermediate with either methanesulfonyl chloride or toluenesulfonyl chloride is pyridine. Thereafter, the mesylate or tosylate is mixed with the appropriate potassium or sodium alkoxide in pyridine, the reaction proceeding smoothly at about 25° C. An equivalent amount of the alkoxide based on the mesylate is preferred to avoid side reactions. In this manner, the formula-XXXIX intermediate is prepared wherein $R_{18}$ is normal alkyl, secondary alkyl, or tertiary alkyl of one to 4 carbon atoms. The method is especially useful for tertiary alkyl substitutions for hydrogen, e.g. wherein $R_{18}$ is tert-butyl.

The formula-XL compound is then obtained in the conventional manner, for example by low temperature reduction with disobutylaluminum hydride as discussed above for Chart B. The final 15-alkyl ether PGFα product XLI is obtained from either XXXIX or XL by the same reactions and condictions discussed above for the steps of Chart B.

Referring to Chart E, there is shown the transformation of lactone XXIX to lactol XLV useful for preparing 15-alkyl-PG-type products. In Chart E, $C_nH_{2n}$, Q, $R_2$, $R_3$, $R_{10}$, and ~ are as defined above for Chart B, $M^{VI}$ is either

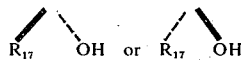

wherein $R_{17}$ is alkyl of one to 4 carbon atoms, inclusive. $M^{VII}$ is either

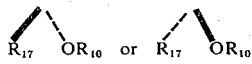

conditions
wherein $R_{17}$ and $R_{10}$ are as defined above.

For the starting material XXIX refer to Chart B and the discussion pertaining thereto. Intermediate XLII is obtained by replacing the side-chain oxo with $M^{VI}$ by a conventional Grignard reaction, employing $R_{17}$MgHal. Next, the acyl group $R_3$ is removed by hydrolysis and the hydrogen atoms of the hydroxyl groups are replaced with blocking groups $R_{10}$ following the procedures of Chart B. Finally lactol XLV is obtained by reduction of lactone XLIV in the same manner discussed above for Charts B and D.

The 15-alkyl products of this invention are obtained from the formula-XLV lactol, following the procedures discussed above for Chart B. The 15 α and 15 β isomers are

CHART E

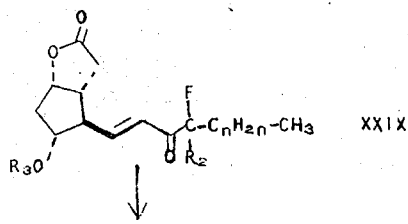

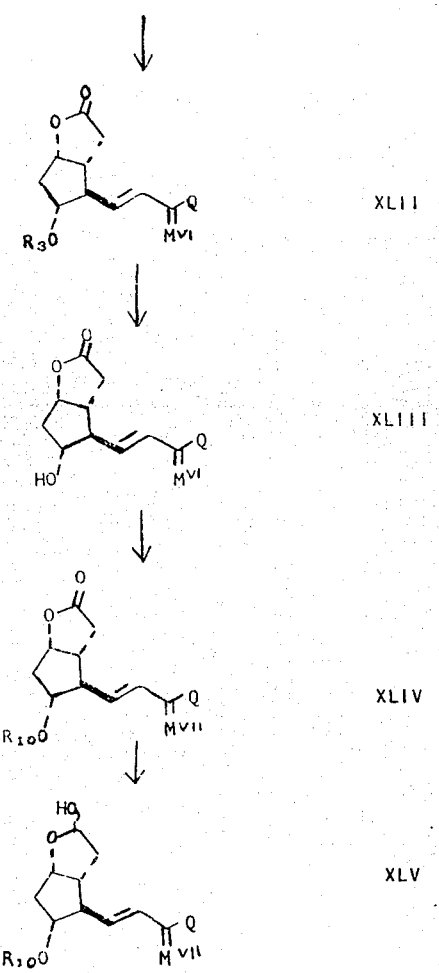

separated by conventional means, for example silica gel chromatography at either the lactol or the final product stages.

Referring to Chart F, there is shown a convenient method for obtaining the 15-alkyl products from corresponding PGF-type compounds shown broadly by formula XLVI. In Chart F, g, M, Q, $R_1$, $R_{17}$, Y, and ~ are as defined above. G is alkyl of one to 4 carbon atoms, inclusive, aralkyl of 7 to 12 carbon atoms, inclusive, phenyl, or phenyl substituted with one or 2 fluoro, chloro, or alkyl of one to 4 carbon atoms, inclusive, and $R_{15}$ is $R_1$ as defined above or silyl of the formula-Si-(G)$_3$ wherein G is as defined above. The various G's of a —Si(G)$_3$ moiety are alike or different. For example, a —Si(G)$_3$ can be trimethylsilyl, dimethyl (t-butyl)silyl, dimethylphenylsilyl, or methylphenylbenzylsilyl. Examples of alkyl of one to 4 carbon atoms, inclusive, are methyl, ethyl, propyl, isopropyl, butyl, isobutyl, sec-butyl, and tert-butyl. Examples of aralkyl of 7 to 12 carbon atoms, inclusive, are benzyl, phenethyl, α-phenylethyl, 3-phenylpropyl, α-naphthylmethyl, and 2-(β-naphthyl)ethyl. Examples or phenyl substituted with one or 2 fluoro, chloro, or alkyl of one to 4 carbon atoms, inclusive are p-chlorophenyl, m-fluorophenyl, o-tolyl, 2,4-dichlorophenyl, p-tert-butylphenyl, 4-chloro-2-methyl-phenyl, and 2,4-dichloro-3-methyl-phenyl.

This method is well-known for preparing 15-alkyl prostaglandins. See South African Pat. No. 2482, May 3, 1972, or Belgian Pat. No. 766,682, Derwent No. 72109S.

CHART F

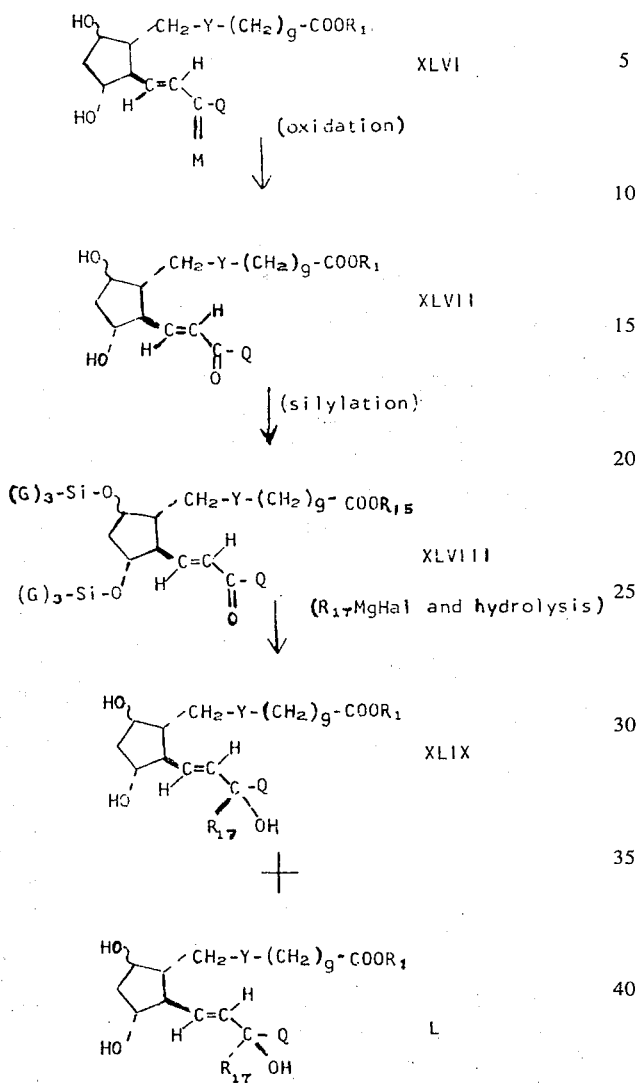

The acids and esters of formula XLVI, available herein by the processes of Charts A through D, are transformed to the corresponding intermediates 15-oxo acids and esters of formula XLVII, respectively, by oxidation with reagents such as 2,3-dichloro-5,6-dicyano-1,4-benzoquinone, activated manganese dioxide, or nickel peroxide (see Fieser et al., "Reagents for Organic Synthesis," John Wiley & Sons, Inc., New York, N.Y., pp. 215, 637 and 731).

Continuing with Chart F, intermediate XLVII is transformed to a silyl derivative of formula XLVIII by procedures known in the art. See, for example, Pierce, "Silylation of Organic Compounds," Pierce Chemical Co., Rockford, Illinois (1968). Both hydroxy groups of the formula-XLVII reactant are thereby transformed to —O—Si—(G)$_3$ moieties wherein G is as defined above, and sufficient of the silylating agent is used for that purpose according to known procedures. When $R_1$ in the formula-XLVII intermediate is hydrogen, the —COOH moiety thereby defined is usually transformed to —COO—Si—(G)$_3$, additional silylating agent being used for this purpose. This latter transformation is aided by excess silylating aent and prolonged treatment. When $R_1$ in formula XLVII is alkyl, then $R_{15}$ in Formula XLVIII will also be alkyl. The necessary silylating agents for these transformations are known in the art or are prepared by methods known in the art. See, for example, Post, "Silicones and Other Silicon Compounds," Reinhold Publishing Corp., New York, N.Y. (1949).

The intermediate silyl compound of formula XLVIII is transformed to the final compounds of formula XLIX + L by first reacting the silyl compound with a Grignard reagent of the formula $R_{17}$MgHal wherein $R_{17}$ is defined as in Chart F, and Hal is chloro, bromo, or iodo. For this purpose, it is preferred that Hal be bromo. This reaction is carried out by the usual procedure for Grignard reactions, using diethyl ether as a reaction solvent and saturated aqueous ammonium chloride solution to hydrolyze the Grignard complex. The resulting disilyl or trisilyl tertiary alcohol is then hydrolyzed with water to remove the silyl groups. For this purpose, it is advantageous to use a mixture of water and sufficient of a water-miscible solvent, e.g., ethanol to give a homogeneous reaction mixture. The hydrolysis is usually complete in 2 to 6 hours at 25° C., and is preferably carried out in an atmosphere of an inert gas, e.g., nitrogen or argon.

The mixture of 15α and 15β isomers obtained by this Grignard reaction and hydrolysis is separated by procedures known in the art for separating mixtures of prostanoic acid derivatives, for example, by chromatography on neutral silica gel. In some instances, the lower alkyl esters, especially the methyl esters of a pair of 15α and 15β isomers are more readily separated by silica gel chromatography than are the corresponding acids. In those cases, it is advantageous to esterify the mixture of acids as described below, separate the two esters, and then, if desired, saponify the esters by procedures known in the art for saponification of prostaglandins F.

Referring to Chart G, there is shown a preferred method of obtaining the 15-alkyl-PGF-type compounds as 15-alkyl ethers. In Chart G, g, M, M''', M$^{VI}$, Q, R$_1$, R$_{10}$, Y and ~ are as defined above. M$^{VIII}$ is either

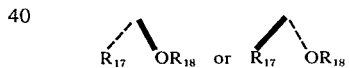

wherein $R_{17}$ and $R_{18}$ are as defined

CHART G

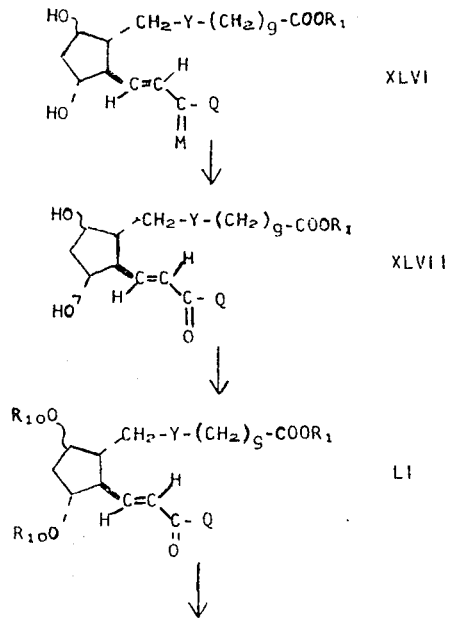

CHART G (continued)

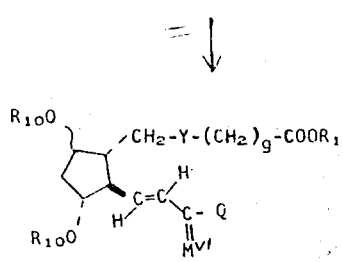
LII

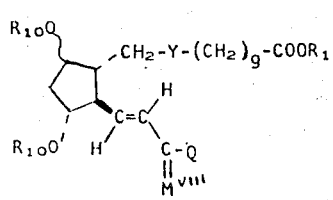
LIII above, i.e. alkyl of one to 4 carbon atoms, inclusive, being the same or different. Starting material XLVI and intermediate XLVII are identical with those of Chart F. Compound LI is obtained by replacing the hydrogen atoms of the C-9 and C-11 hydroxyls with blocking groups $R_{10}$ by the methods discussed above for Chart B. Compound LII is then obtained by replacing the C-15 oxo with $M^{vi}$ by a Grignard reaction, employing $R_{17}MgHal$. Thereafter, compound LIII is obtained by alkylation of the C-15 hydroxy using the methods and reagents discussed above for Chart D, for example diazoalkanes. Finally, the formula-LIII compound is readily transformed to the PGF-type products by hydrolysis of the $R_{10}$ blocking groups. The 15α and 15β isomers are separated by conventional means, for example silica gel chromatography.

The formula-VIII PGE$_1$ and formula XVIII 13,14-dihydro-PGE$_1$ type products of this invention are prepared by ethylenic reduction of the formula-XIII PGE$_2$ type compounds. Reducing agents useful for this transformation are known in the art. Thus, hydrogen is used at atmospheric pressure or low pressure with catalysts such as palladium on charcoal or rhodium on aluminum. See, for example E. J. Corey et al., J. Am. Chem. Soc. 91, 5677 (1969) and B. Samuelsson, J. Biol. Chem. 239, 4091 (1964). For the PGE$_1$ type compounds, the reduction is terminated when one equivalent of hydrogen is absorbed; for the 13,14-dihydro-PGE$_1$ type compounds, when two equivalents are absorbed. For the PGE$_1$-type compounds it is preferred that a catalyst such as nickel boride be used which selectively effects reduction of the cis-5,6-carbon-carbon double bond in the presence of the trans-13,14 unsaturation. Mixtures of the products are conveniently separated by silica gel chromatography.

Alternatively, the bis(tetrahydropyranyl) ethers of the PGE$_2$ type compounds (Formula XXXVI of Chart C) are reduced and subsequently hydrolyzed to remove the tetrahydropyranyl groups.

Chart H shows transformations from he formula-LIV PGE-type compounds to the corresponding PGF-, PGA-, and PGB-type compounds. In figures LIV, LV, LVI, and LVII of Chart H, $C_nH_{2n}$, g, Q, and ∼ have the same meanings as in Chart B; M''' is

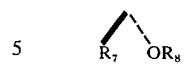

wherein $R_7$ and $R_8$ are hydrogen or alkyl of one to 4 carbon atoms, inclusive, being the same or different; $R_1$ is hydrogen or alkyl of one to 12 carbon atoms, inclusive; cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; and (a) X is trans—CH=CH— or —CH$_2$CH$_2$, and Y is —CH$_2$CH$_2$—, or (b) X is trans—CH=CH— and Y is cis—CH=CH—. When X is trans—CH=CH— and Y is —CH$_2$CH$_2$—, formula LIV represents PGE$_1$ type compounds; when X is —CH$_2$CH$_2$ and Y is —CH$_2$CH$_2$—, formula LIV represents 13,14-dihydro-PGE$_1$ type compounds; and when X is trans—CH=CH— and Y is cis—CH=CH—, formula LIV represents PGE$_2$ type compounds. Thus, formulas LIV, LV, LVI, and LVII embrace all of the compounds represented herein by formulas VIII—XX-III.

Thus, the various PGF$_β$ -type compounds encompassed by formulas X, XV, and XX are prepared by carbonyl reduction of the corresponding PGE-type compounds, e.g. formulas VIII, XIII, and XVIII. For example, carbonyl reduction of

CHART H

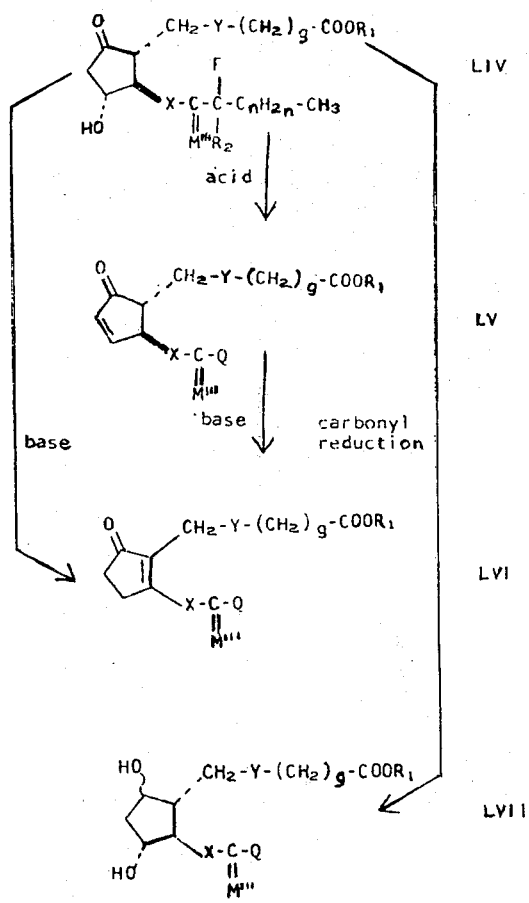

16-fluoro-19,20-dinor-PGE$_1$ gives a mixture of 16-fluoro-19,20-dinor-PGF$_{1\alpha}$ and 16-fluoro-19,20-dinor-PGF$_{1\beta}$.

These ring carbonyl reductions are carried out by methods known in the art for ring carbonyl reductions of known prostanoic acid derivatives. See, for example, Bergstrom et al., Arkiv Kemi 19, 563 (1963), Acta. Chem. Scand. 16, 969 (1962), and British Specification No. 1,097,533. Any reducing agent is used which does not react with carbon-carbon double bonds or ester groups. Preferred reagents are lithium(tri-tert-butoxy)aluminum hydride, the metal borohydrides, especially sodium, potassium and zinc borohydrides, the metal trialkoxy borohydrides, e.g., sodium trimethoxyborohydride. The mixtures of alpha and beta hydroxy reduction products are separated into the individual alpha and beta isomers by methods known in the art for the separation of analogous pairs of known isomeric prostanoic acid derivatives. See, for example, Bergstrom et al., cited above, Granstrom et al., J. Biol. Chem. 240, 457 (1965), and Green et al., J. Lipid Research 5, 117 (1964). Especially preferred as separation methods are partition chromatographic procedures, both normal and reversed phase, preparative thin layer chromatography, and countercurrent distribution procedures.

The various PGA-type compounds encompassed by formulas XI, XVI, and XXI are prepared by acidic dehydration of the corresponding PGE-type compounds, e.g. formulas VIII, XIII, and XVIII. For example, acidic dehydration of 16-fluoro-PGE$_2$ gives 16-fluoro-PGA$_2$.

These acidic dehydrations are carried out by methods known in the art for acidic dehydrations of known prostanoic acid derivatives. See, for example, Pike et al., Proc. Nobel Symposium II, Stockholm (1966), Interscience Publishers, New York, pp. 162–163 (1967); and British Specification 1,097,533. Alkanoic acids of 2 to 6 carbon atoms, inclusive, especially acetic acid, are preferred acids for this acidic dehydration. Dilute aqueous solutions of mineral acids, e.g., hydrochloric acid, especially in the presence of a solubilizing diluent, e.g., tetrahydrofuran, are also useful as reagents for this acidic dehydration, although these reagents may cause partial hydrolysis of an ester reactant.

The various PGB-type compounds encompassed by formulas XII, XVII, and XXII are prepared by basic dehydration of the corresponding PGE-type compounds encompassed by formulas VIII, XIII, and XVIII or by contacting the corresponding PGA-type compounds encompassed by formulas XI, XVI, and XXI with base. For example, both 16,16-difluoro-13,14-dihydro-PGE$_1$ and 16,16-difluoro-13,14-dihydro-PGA$_1$ give 16,16-difluoro-13,14-dihydro-PGB$_1$ on treatment with base.

These basic dehydrations and double bond migrations are carried out by methods known in the art for similar reactions of known prostanoic acid derivatives. See, for example, Bergstrom et al., J. Biol. Chem. 238, 3555 (1963). The base is any whose aqueous solution has pH greater than 10. Preferred bases are the alkali metal hydroxides. A mixture of water and sufficient of a water-miscible alkanol to give a homogeneous reaction mixture is suitable as a reaction medium. The PGE-type or PGA-type compound is maintained in such a reaction medium until no further PGB-type compound is formed, as shown by the characteristic ultraviolet light absorption near 278 m$\mu$ for the PGB-type compound.

Optically active compounds are obtained from optically active intermediates according to the process steps of Charts A, B, D, and E. Likewise, optically active products are obtained by the transformations of optically active compounds following the processes of Charts C, F, G, and H. When racemic compounds are used in reactions corresponding to the processes of Charts A—H, inclusive, and racemic products are obtained, these racemic products may be used in their racemic form or, if preferred, they may be resolved as optically active isomers by procedures known in the art.

For example, when final compound VIII to XXIII is a free acid, the dl form thereof is resolved into the d and l forms by reacting said free acid by known general procedures with an optically active base, e.g., brucine or strychnine, to give a mixture of two diastereoisomers which are separated by known general procedures, e.g., fractional crystallization, to give the separate diastereoisomeric salts. The optically active acid of formula VIII to XXIII is then obtained by treatment of the salt with an acid by known general procedures.

As discussed above, the stereochemistry at C-15 is not altered by the transformations of Charts A and B; the 15$\beta$ epimeric products of formula XXXV are obtained from 15$\beta$ formula-XXX reactants. Another method of preparing the 15$\beta$ products is by isomerization of the PGF$_1$- or PGE$_1$-type compounds having 15$\alpha$ configuration, by methods known in the art. See, for example, Pike et al., J. Org. Chem. 34, 3552 (1969).

When the processes of Charts B-H yield an ester, such as where R$_1$ is methyl, the free acid products are obtained by methods known in the art. For example, the 16-fluoro-PGF$_2$ analogs are subjected to sapenification in an aqueous alkaline medium to form an alkaline salt, which is then acidified to yield the free acid. A preferred method for the 16-fluoro-PGE$_2$ analogs, and useful for the 16-fluoro-PGF$_2$ analogs as well, is by enzymatic hydrolysis using an esterase enzyme composition obtained from the marine invertebrate Plexaura homomalla (Esper), 1792. *Plexaura homomalla* is a member of the sub-class Octocorallia, order Gorgonacea, suborder Holaxonia, family Plexauridae, genus Plexaura. See, for example, Bayer, "The Shallow-Water Octocorallia of the West Indian Region", Martinus Nijhoff, The Hague (1961). Colonies of these Plexaura homomalla are abundant on the ocean reefs in the zone from low-tide line to about 25 fathoms in the tropical and subtropical regions of the western part of the Atlantic Ocean, from Bermuda to the reefs of Brazil, including the eastern shore reefs of Florida, the Caribbean island and mainland reefs, and the Gulf of Mexico island and mainland reefs. These colonies are bush-like or small tree-like in habit and are readily identified for collection as Plexaura homomalla (Esper), 1792, by those of ordinary skill in this art. Two forms exist, the "R" form and the "S" form. See W. P. Schneider et al., J. Am. Chem. Soc. 94, 2122 (1972).

The esterase enzyme composition is produced by the steps: (1) extracting colonies or colony pieces of the marine invertebrate Plexaura homomalla (Esper), 1792, forma R or forma S, with liquid acetone for a sufficient time to remove substantially all soluble lipids, and (2) recovering the acetone-insoluble matter as said composition.

The colonies of *Plexaura homomalla* are used either in their as-harvested form or in broken or chopped pieces. It is immaterial whether they are used fresh from their natural environment, or after freezing and thawing, or even after drying under ambient conditions.

The extraction with acetone may be done batch-wise, as by stirring in a container, or by percolation, or by continuous methods of extraction known in the art. If stirring is used, it is advantageous to first chop the Plexaura homomalla into small pieces, for example less than 3 mm. in greatest dimension. The product is accordingly then a powder consisting of pieces smaller than 3 mm. Contact with acetone is continued until substantially all of the soluble lipids are removed. Normally 1 hour is sufficient, although a longer time is required for whole colonies and a shorter time is sufficient for chopped colonies with efficient extraction. The end-point can be determined simply by examination of the acetone, as by evaporation and by physical measurements on any residue thus obtained. The extraction temperature is kept below 50° C. to avoid denaturation of the enzyme, and is preferably in the range 20° to 30° C. Lower temperatures may be used but the extraction then proceeds more slowly. The extraction is generally done at atmospheric pressure, but it may be carried out at higher or lower pressures provided the acetone is in a liquid state when contacting the *Plexaura homomalla*.

The acetone-insoluble enzyme composition is recovered from the acetone by decantation, filtration, centrifugation, or other convenient method for separating solids and liquids. A small amount of adherent acetone, for example, 10% of the weight of the composition, may be left on the product but it is preferred that the amount be lowered to less than 1%, for example by drying under ambient conditions or under reduced pressure. The product can then be stored without deterioration, preferably at about −20° C.

In utilizing the above esterase enzyme composition for the purposes of this invention, the 5-oxa prostaglandin ester is contacted with a mixture of the enzyme composition and water. The ester is conveniently added as a solution, for example in ethanol or benzene, to about 50–100 times its weight of water. The enzyme composition is added in an amount about 1–15 times the weight of ester. The mixture is stirred until the ester is hydrolyzed, generally about 18–24 hours at 25° C. Temperatures of about 0°–50° C. may be employed, although about 25° C. is preferred. The progress of hydrolysis is readily followed by analysis, for example by thin-layer chromatography by methods known in the art. See, for example, Hamberg et al., J. Biol. Chem. 241, 257 (1966). Finally, several volumes of acetone are added and the soluble acid products are recovered by filtration, concentration, and extraction using methods known in the art.

As discussed above, the processes of Charts B–H inclusive, lead variously to acids ($R_1$ is hydrogen) or to esters ($R_2$ is alkyl, cycloalkyl, aralkyl, phenyl or substituted phenyl, as defined above). When an acid has been prepared and an alkyl ester is desired, esterification is advantageously accomplished by interaction of the acid with the appropriate diazohydrocarbon. For example, when diazomethane is used, the methyl esters are produced. Similar use of diazoethane, diazobutane, and 1-diazo-2-ethylhexane, and diazodecane, for example, gives the ethyl, butyl, and 2-ethylhexyl and decyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reactions, John Wiley and Sons, Inc., New York, N.Y., Vol. 8, pp. 389–394 (1954).

An alternative method for esterification of the carboxyl moiety of the acid compounds comprises transformation of the free acid to the corresponding silver salt, followed by interaction of that salt with an alkyl iodide. Examples of suitable iodides are methyl iodide, ethyl iodide, butyl iodide, isobutyl iodide, tert-butyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

The final formula VIII-to-XXIII compounds prepared by the processes of this invention, in free acid form, are transformed to pharmacologically acceptable salts by neutralization with appropriate amounts of the corresponding inorganic or organic base, examples of which correspond to the cations and amines listed above. These transformations are carried out by a variety of procedures known in the art to be generally useful for the preparation of inorganic, i.e., metal or ammonium, salts, amine acid addition salts, and quaternary ammonium salts. The choice of procedure depends in part upon the solubility characteristics of the particular salt to be prepared. In the case of the inorganic salts, it is usually suitable to dissolve the formula VIII-to-XXIII acid in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, the formula VIII-to-XXIII acid is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing the formula VIII-to-XXIII acid with the stoichiometric amount of the corresponding quaternary ammonium hydroxide in water solution, followed by evaporation of the water.

The final formula VIII-to-XXIII acids or esters prepared by the processes of this invention are transformed to lower alkanoates by interaction of the formula VIII-to-XXIII hydroxy compound with a carboxyacylating agent, preferably the anhydride of a lower alkanoic acid, i.e., an alkanoic acid of two to 8 carbon atoms, inclusive. For example, use of acetic anhydride gives the corresponding acetate. Similar use of propionic anhydride, isobutyric anhydride, and hexanoic acid anhydride gives the corresponding carboxyacylates.

The carboxyacylation is advantageously carried out by mixing the hydroxy compound and the acid anhydride, preferably in the presence of a tertiary amine such as pyridine or triethylamine. A substantial excess of the anhydride is used, preferably about 10 to about 10,000 moles of anhydride per mole of the hydroxy compound reactant. The excess anhydride serves as a reaction diluent and solvent. An inert organic diluent, for example, dioxane, can also be added. It is preferred to use enough of the tertiary amine to neutralize the carboxylic acid produced by the reaction, as well as any free carboxyl groups present in the hydroxy compound reactant.

The carboxyacylation reaction is preferably carried out in the range about 0° to about 100° C. The necessary reaction time will depend on such factors as the reaction temperature, and the nature of the anhydride and tertiary amine reactants. With acetic anhydride, pyridine, and a 25° C. reaction temperature, a 12 to 24-hour reaction time is used.

The carboxyacylated product is isolated from the reaction mixture by conventional methods. For example, the excess anhydride is decomposed with water, and the resulting mixture acidified and then extracted with a solvent such as diethyl ether. The desired carboxyacylate is recovered from the diethyl ether extract by evaporation. The carboxyacylate is then purified by conventional methods, advantageously by chromatography.

By this procedure, the formula VIII, XIII, and XVIII PGE-type compounds are transformed to dialkanoates, the formula IX, X, XIV, XV, XIX, and XX PGF-type compounds are transformed to trialkanoates, and the formula XI, XVI, and XXI PGA-type and formula XII, XVII, and XXII PGB-type compounds are transformed to monoalkanoates.

When a PGE-type dialkanoate is transformed to a PGF-type compound by carbonyl reduction as shown in Chart S, a PGF-type dialkanoate is formed and is used for the above-described purposes as such or is transformed to a trialkanoate by the above-described procedure. In the latter case, the third alkanoyloxy group can be the same as or different from the two alkanoyloxy groups present before the carbonyl reduction.

DESCRIPTION OF THE PREFERRED EMBODIMENTS

The invention can be more fully understood by the following examples.

All temperatures are in degrees centigrade.

Infrared absorption spectra are recorded on a Perkin-Elmer model 421 infrared spectrophotometer. Except when specified otherwise, undiluted (neat) samples are used.

Mass spectra are recorded on an Atlas CH-4 mass spectrometer with a TO-4 source (ionization voltage 70 ev).

NMR spectra are recorded on a Varian A-60 spectrophotometer in deuterochloroform solutions with tetramethylsilane as an internal standard (downfield).

"Brine", herein, refers to an aqueous saturated sodium chloride solution.

PREPARATION 1

3α-Benzoyloxy-2β-carboxaldehyde-5α-hydroxy-1α-cyclopentaneacetic Acid γ-Lactone (Formula XXVIII: $R_3$ is benzoyl).

Refer to Chart A. a. To a mixture of formula-XXIV laevorotatory (−) 3α-hydroxy-5α-hydroxy-4-iodo-2β-methoxymethyl- 1α-cyclopentaneacetic acid γ-lactone (E. J. Corey et al., J. Am. Chem. Soc. 92, 397 (1970), 75 g.) in 135 ml. of dry pyridine under a nitrogen atmosphere is added 30.4 ml. of benzoyl chloride with cooling to maintain the temperature at about 20°–40° C. Stirring is continued for an additional 30 min. About 250 ml. of toluene is added and the mixture concentrated under reduced pressure. The residue is dissolved in one liter of ethyl acetate, washed with 10% sulfuric acid, brine, aqueous saturated sodium bicarbonate, and brine. The ethyl acetate solution is dried over sodium sulfate and concentrated under reduced pressure to yield an oil, 95 g. Crystallization of the oil yields the corresponding 3α-benzoyloxy compound, m. p. 84°–86° C.; $[\alpha]_D + 7°$ (CHCl$_3$); infrared spectral absorptions at 1768, 1722, 1600, 1570, 1490, 1275, 1265, 1180, 1125, 1090, 1060, 1030, and 710 cm$^{-1}$; and NMR (nuclear magnetic resonance) peaks at 2.1–45, 3.3, 3.58, 4.38, 5.12, 5.51, 7.18–7.58, and 7.83–8.05 δ.

b. The iodo group is removed as follows. To a solution of the above benzoyloxy compound (60 g.) in 240 ml. of dry benzene is added 2,2′-azobis-(2-methylpropionitrile) (approximately 60 mg.). The mixture is cooled to 15° C. and to it is added a solution of 75 g. tributyltin hydride in 600 ml. of ether, with stirring, at such a rate as to maintain continuous reaction at about 25° C. When the reaction is complete as shown by TLC (thin layer chromatography), the mixture is concentrated under reduced pressure to an oil. The oil is mixed with 600 ml. of Skellysolve B (mixed isomeric hexanes) and 600 ml. of water and stirred for 30 min. The water layer, containing the product, is separated, then combined with 450 ml. of ethyl acetate and enough solid sodium chloride to saturate the aqueous phase. The ethyl acetate layer, now containing the product, is separated, dried over magnesium sulfate, and concentrated under reduced pressure to an oil, 39 g. of the iodine-free compound. An analytical sample gives $[\alpha]_D −99°$ (CHCl$_3$); infrared spectral absorptions at 1775, 1715, 1600, 1585, 1490, 1315, 1275, 1180, 1110, 1070, 1055, 1025, and 715 cm$^{-1}$.; NMR peaks at 2.5–3.0, 3.25, 3.34, 4.84–5.17, 5.17–5.4, 7.1–7.5, and 7.8–8.05 δ; and mass spectral peaks at 290, 168, 105, and 77.

c. The 2β-methoxymethyl compound is changed to a hydroxymethyl compound as follows. To a cold (0.5° C.) solution of the above iodine-free methoxy-methyl lactone (20 g.) in 320 ml. of dichloromethane under nitrogen is added a solution of 24.8 ml. of boron tribromide in 320 ml. of dichloromethane, dropwise with vigorous stirring over a period of 50 min. at 0°–5° C. Stirring and cooling are continued for 1 hr. When the reaction is complete, as shown by TLC, there is cautiously added a solution of sodium carbonate (78 g. monohydrate) in 200 ml. of water. The mixture is stirred at 0°–5° C. for 10–15 min., saturated with sodium chloride, and the ethyl acetate layer separated. Additional ethyl acetate extractions of the water layer are combined with the main ethyl acetate solution. The combined solutions are rinsed with brine, dried over sodium sulfate and concentrated under reduced pressure to an oil, 18.1 g. of the 2β-hydroxymethyl compound. An analytical sample has m.p. 116°–118° C.; $[\alpha]_D$ −80° ($CHCl_3$); infrared spectral absorptions at 3460, 1735, 1708, 1600, 1580, 1490, 1325, 1315, 1280, 1205, 1115, 1090, 1070, 1035, 1025, 730, and 720; and NMR peaks at 2.1–3.0, 3.58, 4.83–5.12, 5.2–5.45, 7.15–7.55, and 7.8–8.0 δ.

d. The title 2β-carboxaldehyde compound is prepared as follows. To a mixture of 150 ml. of dry dichloromethane and Collins' reagent (J. C. Collins et al., Tetrahedron Lett. 3363 (1968), 28 g.) at about 10° C. under nitrogen is added, with vigorous stirring, a cold (10° C.) solution of the hydroxymethyl compound above (5.0 g.) in 150 ml. of dichloromethane. After 5 min. additional stirring, about 100 ml. of dry benzene is added, the mixture is filtered, and the solution is concentrated under reduced pressure. The volume is brought to about 150 ml. with benzene. The solution of the formula-XXVIII title compound is used directly. In a repetitive experiment the Collins' reagent is prepared in situ with comparable results.

Following the procedure of Preparation 1, but replacing that optically active formula-XXIV iodolactone with the racemic compound of that formula and the mirror image thereof (see E. J. Corey et al., J. Am. Chem. Soc. 91, 5675 (1969)) there is obtained the racemic compound corresponding to formula XXVIII.

PREPARATION 2

5-Carboxypentyltriphenylphosphonium Bromide.

A mixture of 6-bromohexanoic acid (50 g.), triphenylphosphine (67.1 g.) and 240 ml. of acetonitrile is heated at reflux for 22 hr. Then 160 ml. of acetonitrile is removed by distillation. The solution is cooled and to it is added 240 ml. of benzene. The title compound is obtained as crystals, m.p. 201°–203° C.; infrared spectral absorptions at 2800, 1705, 1585, 1480, 1435, 1375, 1225, 1210, 1190, 1115, 745, 725, and 695 cm.$^{-1}$; and NMR peaks at 1.5–1.9, 2.2–2.6, 3.3–4.0 and 7.7–8.0 (multiplet) δ.

PREPARATION 3

6-Carboxyhexyltriphenylphosphonium Bromide

Following the procedure of Preparation 2, but using 7-bromoheptanoic acid instead of 6-bromohexanoic acid, the title compound is obtained as crystals, m. p. 185°–187° C.; infrared spectral absorptions at 2850, 2570, 2480, 1710, 1585, 1485, 1235, 1200, 1185, 1160, 1115, 1000, 755, 725, and 695 cm.$^{-1}$; and NMR peaks at 1.2–1.9, 2.1–2.6, 3.3–4.0, and 7.7–8.0 (multiplet) δ.

EXAMPLE 1

3α-Benzoyloxy-5α-hydroxy-2β-(3-oxo-4-fluoro-trans-1-octenyl)-1α-cyclopentaneacetic Acid γ-Lactone (Formula XXIX: $C_nH_{2n}$ is —$(CH_2)_3$—, $R_2$ is hydrogen, and $R_3$ is benzoyl).

Refer to Chart B. a. There is first prepared dimethyl 2-oxo-3-fluoroheptylphosphonate. Ethyl 2-fluorohexanoate (prepared from 2-fluorohexanoic acid and diazoethane by known methods, 37 g.) is added to a mixture of dimethyl methylphosphonate (62 g.) and butyllithium (312 ml. of 1.6 M. solution) in 600 ml. of tetrahydrofuran previously cooled to −70° C. The reaction mixture is stirred for 2 hrs., then acidified with acetic acid and concentrated under reduced pressure. The residue is partitioned between dichloromethane and water. The organic phase is dried, concentrated, and distilled to yield the desired product, b.p. 116°–117° C./0.2 mm., 46.9 g.

b. A solution of the formula-XXVIII 3α-benzoyloxy-2β-carboxaldehyde-5α-hydroxy-1α-cyclopentaneacetic acid γ-lactone (Preparation 1, 3.0 g.) in 30 ml. of dichloromethane is added to a solution of the anion of dimethyl 2-oxo-3-fluoroheptylphosphonate prepared from that compound (part 1, above, 6.69 g.) and sodium hydride (1.35 g.) in 50 ml. of tetrahydrofuran. The resulting reaction mixture is stirred for 2 hr. at about 25° C., then acidified with acetic acid and concentrated under reduced pressure. The residue is partitioned between dichloromethane and water, and the organic phase is concentrated. The residue is chromatographed on silica gel, eluting with ethyl acetate-Skellysolve B (isomeric hexanes) (1:1). The product has m.p. 90°–93° C.; mass spectral peaks at 388, 368, and 299; infrared absorption peaks at 1780, 1725, 1670, 1640, 1550, 1420, 1190, 1110 and 985 cm.$^{-1}$.

The racemic phosphonate used in Example 1-a yields a mixture of 4-fluoro epimers, i.e. diastereomers, corresponding to the formula-XXIX title compound which are separated by conventional methods, e.g. by silica gel chromatography.

Following the procedure of Example 1 but replacing racemic ethyl 2-fluorohexanoate with the ethyl esters of the (+) and (−) isomers of 2-fluorohexanoic acid obtained by resolution of the racemic acid, there are obtained the corresponding optically active (+) and (−) phosphonates and, thence, the corresponding optically active title compounds.

Following the procedure of Example 1, but replacing the optically active formula-XXVIII aldehyde with the racemic aldehyde obtained after Preparation 1, and using the racemic phosphonate of Example 1-b, there are obtained two pairs of 3-oxo-4-fluoro racemates which are separable into pairs of racemic compounds by methods known in the art, e.g. silica gel chromatography.

Following the procedure of Example 1, but using the racemic aldehyde above with the optically active (+) and (−) phosphonates above, there are obtained a corresponding pair of diastereomers from each, which are separable into their separate isomers, e.g. by silica gel chromatography.

Likewise following the procedure of Example 1, but replacing racemic ethyl 2-fluorohexanoate with each of the following aliphatic acid esters there are obtained the corresponding phosphonates, with optically active esters yielding optically active phosphonates and racemic esters yielding racemic phosphonates, and thence the optically active or racemic lactones corresponding to formula-XXIX wherein $R_3$ is benzoyl:

methyl 2-fluorobutyrate
ethyl 2,2-difluorobutyrate
methyl 2-fluoro-2-methylbutyrate
ethyl 2-fluorovalerate
ethyl 2-ethyl-2-fluorovalerate
methyl 2,2-difluorohexanoate
methyl 2-fluoro-3-methylhexanoate
ethyl 2,3-diethyl-2-fluorohexanoate
ethyl 4-ethyl-2-fluorohexanoate
methyl 2-fluoroheptanoate
methyl 2-fluoro-6-methylheptanoate
methyl 2,2-difluoro-3-methylheptanoate
ethyl 2-fluorooctanoate
methyl 2,2-difluorononanoate
methyl 2-fluoro3-propylnonanoate For example, methyl 2-fluorobutyrate yields dimethyl 2-oxo-3-fluoropentylphosphonate and, thence, the formula-XXIX 3α-benzoyloxy-5α-hydroxy-2β-(3-oxo-4-fluoro-trans-1-hexenyl)-1α-cyclopentaneacetic acid γ-lactone. Likewise, methyl 2,2-difluoro-3-methylheptanoate yields dimethyl 2-oxo-3,3-difluoro-4-methyloctylphosphonate, and, thence, the formula-XXIX 3α-benzoyloxy-5α-hydroxy-b 2β-(3-oxo-4,4-difluoro-5-methyl-trans-1-nonenyl)-1α-cyclopentaneactic acid γ-lactone.

EXAMPLE 2

3α-Benzoyloxy-5α-hydroxy-2β-(3α-hydroxy-4-fluoro-trans-1-octenyl)-1α-cyclopentaneacetic Acid γ-Lactone (Formula XXX: M is

Q is

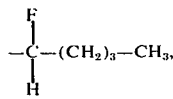

and $R_3$ is benzoyl) ; and the 3β-hydroxy isomer (Formula XXX: M is

Refer to Chart B. A mixture of sodium borohydride (0.17 g.) and zinc chloride (0.76 g.) in 7 ml. of the dimethyl ether of 1,2-ethanediol is stirred at about 25° C. for 2.5 hr. Then a solution of the formula-XXIX 3-oxo-4-fluoro compound (Example 1, 0.44 g.) in 4 ml. of the dimethyl ether of 1,2-ethanediol is added and the mixture is stirred for 2.5 hr. Finally, 3 ml. of water and 20 ml. of ethyl acetate are added, the solids filtered off, and the liquid washed with brine. The organic phase is concentrated under reduced pressure to an oil, 0.57 g. This material is chromatographed over silica gel, eluting with ethyl acetate-Skellysolve B (1:1) and collecting fractions of 4 ml. each. Fractions No. 85–105 are combined and concentrated to yield the formula-XXX 3α-hydroxy compound, 0.14 g. Likewise, fractions No. 111–129 are combined and concentrated to yield the formula-XXX 3β-hydroxy isomer, 0.13 g.

Following the procedure of Example 2, but using the racemic 3-oxo-4-fluoro compounds obtained following Example 1, there are obtained the corresponding racemic 3-hydroxy products.

Likewise following the procedure of Example 2, each of the optically active or racemic lactones corresponding to formula XXIX described following Example 1 is transformed to the optically active or racemic compound corresponding to formula XXX.

EXAMPLE 3

3α,5α-Dihydroxy-2β-(3α-hydroxy-4-fluoro-trans-1-octenyl)-1α-cyclopentaneacetaldehyde γLactol Bis(tetrahydropyranyl) Ether (Formula XXXIII: M' is

Q is

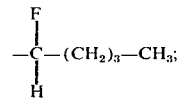

$R_{10}$ is tetrahydropyranyl; and ~ is alpha or beta).

1. Refer to Chart B. A solution of the formula-XXX 3α-hydroxy-4-fluoro compound (Example 2, 0.9 g.) and potassium carbonate (0.32 mg.) in 20 ml. of anhydrous methanol is stirred at 26° C. for 1 hr. under nitrogen and then diluted with 25 ml. of 1,2-dichloroethane. The solution is washed with brine, filtered through sodium sulfate, and concentrated under reduced pressure. The oily residue is triturated with several portions of Skellysolve B, and dried to yield the formula-XXXI benzoyloxy-free compound, namely 3α,5α-dihydroxy-2β-(3α-hydroxy-4-fluoro-trans-2-octenyl)-1α-cyclopentaneacetic acid γ-lactone, 0.546 g. Additional product (0.122 g.) is recovered from the aqueous wash by acidifying with potassium hydrogen sulfate and extracting with dichloromethane.

2. The formula-XXXI compound from part 1 above (0.668 g.) is converted to the bis(tetrahydropyranyl) ether by reaction with 1.8 ml. of dihydropyran in 10 ml. of dichloromethane in the presence of pyridine hydrochloride (11 mg.) The reaction mixture is washed with dilute aqueous potassium bicarbonate, dried and concentrated to the formula-XXXII bis(tetrahydropyranyl) ether, 1.23 g. 3. The title compound is prepared as follows. Diisobutylaluminum hydride (0.82 ml. in 4 ml. of toluene) is added dropwise to a stirred solution of the formula-XXXII bis(tetrahydropyranyl)ether from part 2 above (1.23 g.) in 10 ml. of toluene cooled to −78°C. Stirring is continued at −78° C. for 1 hrs., whereupon a solution of 2 ml. of tetrahydrofuran and 1 ml. of water is added cautiously. After the mixture is stirred an additional 0.5 hr. at about 25° C., it is diluted with benzene and filtered. The filtrate is washed with brine, dried, and concentrated to the mixed alpha and beta hydroxy isomers of the formula-XXXIII title compounds, 1.2 g., showing no lactone by TLC.

Likewise following the procedure of Example 3, but using the formula-XXX 3β-hydroxy-4-fluoro isomer of Example 2, there is obtained the corresponding 3β-hydroxy formula-XXXIII compound, i.e. wherein M' is

Following the procedures of Example 3, each of the optically active or racemic compounds corresponding to formula XXX described following Example 2 is transformed to an optically active or racemic compound corresponding to formula XXXIII. There are thus obtained both the 3α-and 3β-hydroxy isomers of XXXIII.

EXAMPLE 4

16-Fluoro-PGF$_{2\alpha}$, 11,15-Bis (tetrahydropyranyl) Ether (Formula XXXIV: M' is

and

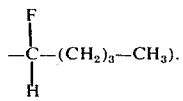

Refer to Chart B. 4-Carboxybutyltriphenylphosphonium bromide (E.J. Corey et al., J. Am. Chem. Soc. 91, 5677 (1969) (4.43 g.) is added to a solution of sodio dimethylsulfinylcarbanide prepared from sodium hydride (57%, 0.84 g.) and 14 ml. of dimethylsulfoxide (DMSO). To this reagent is added dropwise a solution of the formula-XXXIII lactol of Example 3 in 6 ml. of DMSO. The mixture is stirred at about 25° C. for 2 hr., then diluted with 80 ml. of benzene. To the mixture is added, with stirring, a solution of potassium hydrogen sulfate (4.08 g.) in 20 ml. of water. The organic layer is separated, washed with water, dried, and concentrated under reduced pressure. The residue is triturated with diethyl ether and cooled to 10° C. Crystals which form are separated and discarded. The liquid residue after evaporation is chromatographed on silica gel, eluting with chloroform-methanol (10:1) and combining those fractions shown by TLC to contain the product free of starting material and impurities. Concentration under reduced pressure yields the title compound, 0.82 g.

EXAMPLE 5

16-Fluoro-PGF$_{2\alpha}$ (Formula XIV: C$_n$H$_{2n}$ is —(CH$_2$)$_3$—, g is 3, M''' is

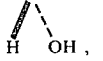

and R$_1$ and R$_2$ are hydrogen).

Refer to Chart B. A solution of the formula-XXXIV bis(tetrahydropyranyl) ether (Example 4, 0.37 g.) in 1.5 ml. of acetonitrile is mixed with 15 ml. of 66% acetic acid. The mixture is heated at about 46° C. for 1.5 hr. and then concentrated under reduced pressure. The residue is taken up in toluene and again concentrated. The residue is chromatographed on silica gel, eluting with ethyl acetate-acetone-water (8:5:1). Those fractions shown by TLC to contain the product free of starting material and impurities are combined and concentrated to yield the title compound, 0.16 g.: mass spectral peaks at 645, 640, 597 571 and 550, and infrared absorption peaks at 3400, 2950, 2550, 1720, and 1440 cm$^{-1}$.

Following the procedures of Examples 4 and 5, each of the optically active or racemic 3α-hydroxy compounds corresponding to formula XXXIII described following Example 3 is transformed to the co-responding bis(tetrahydropyranyl) ether and thence to the corresponding 16- (or 16,16-di-) fluoro-PGF$_{2\alpha}$ type compound or racemic mixture. There are thus obtained the following compounds from the 3α-hydroxy isomers:

16-fluoro-19,20-dinor-PGF$_{2\alpha}$
16,16-difluoro- 19,20-dinor-PGF$_{2\alpha}$
16-fluoro-16-methyl-19,20-dinor-PGF$_{2\alpha}$
16-fluoro-20-nor-PGF$_{2\alpha}$
16-ethyl-16-fluoro-20-nore-PGF$_{2\alpha}$
16,16-difluoro-PGF$_{2\alpha}$
16-fluoro-16-methyl-PGF$_{2\alpha}$
16,17-diethyl-16-fluoro-PGF$_{2\alpha}$
18-ethyl-16-fluoro-PGF$_{2\alpha}$
16-fluoro-20-methyl-PGF$_{2\alpha}$
16-fluoro-20,20-dimethyl-PGF$_{2\alpha}$
16,16-difluoro-17,20-dimethyl-PGF$_{2\alpha}$
16-fluoro-20 -ethyl-PGF$_{2\alpha}$
16,16-difluoro-20-propyl-PGF$_{2\alpha}$
16-fluoro-17,20-dipropyl-PGF$_{2\alpha}$ and their racemic mixtures, for example dl-16-fluoro-19,20-dinor-PGF$_{2\alpha}$. From the 3β-hydroxy compounds corresponding to formula XXXIII are obtained the corresponding 15β epimers and their racemic mixtures, for example:

16-fluoro-15β-PGF$_{2\alpha}$
16,16-difluoro-19,20-dinor-15β-PGF$_{2\alpha}$ and
dl-16-fluoro-16-methyl-19,20-dinor-15β-PGF$_{2\alpha}$

EXAMPLE 6

16-Fluoro-2-nor-PGF$_{2\alpha}$ (Formula XIV: C$_n$H$_{2n}$ is —(CH$_2$)$_3$—, g is 2, M''' is

and R$_1$ and R$_2$ are hydrogen).

Refer to Chart B. Following the procedures of Examples 4 and 5 but replacing 4-carboxybutyltriphenylphosphonium bromide with 3-carboxypropyltriphenylphosphonium chloride (D.B. Denny et al., J. Org. Chem. 27, 3404 (1962)), there is obtained the formula-XXXIV 16-fluoro-2-nor-PGF$_{2\alpha}$, bis(tetrahydropyranyl) ether, and thence the title compound.

EXAMPLE 7

16-Fluoro-2α-homo-PGF$_{2\alpha}$. (Formula XIV: C$_n$H$_{2n}$ is —(CH$_2$)$_3$—, g is 4, M''' is

and R$_1$ and R$_2$ are hydrogen).

Following the procedures of Examples 4 and 5 but replacing 4-carboxybutyltriphenylphosphonium bromide with 5-carboxypentyltriphenylphosphonium bromide, (Preparation 2), there are obtained the title compound and the corresponding bis(tetrahydropyranyl)ether.

EXAMPLE 8

16-Fluoro-2a,2b-dihomo-PGF$_{2\alpha}$ (Formula XIV: C$_n$H$_{2n}$ is —(CH$_2$)$_3$—, g is 5, M''' is

and R$_1$ and R$_2$ are hydrogen).

Following the procedures of Examples 4 and 5 but replacing 4-carboxybutyltriphenylphosphonium bromide with 6-carboxyhexyltriphenylphosphonium bromide (Preparation 3) there are obtained the title compound and the corresponding bis(tetrahydropyranyl) ether.

Following the procedures of Examples 4 and 5, and employing each of the carboxyalkyltriphenylphosphonium halide reactants of Examples 6, 7, and 8, each of the optically active or racemic 3α-hydroxy compounds corresponding to formula XXXIII described following Example 3 is transformed to the corresponding bis(tetrahydropyranyl) ether wherein the carboxy-terminated side chain has six; eight, or nine carbon atoms and thence, to the corresponding 16-(or 16,16-di)fluoro-PGF$_{2\alpha}$ type compound or racemic mixture, for example:

16-fluoro-2,19,20-trinor-PGF$_{2\alpha}$
16,16-difluoro-2α-homo-19,20-dinor-PGF$_{2\alpha}$
16-fluoro- 16-methyl-2a,2b-dihomo-19,20-dinor-PGF 2α
16-fluoro-2,20-dinor-PGF$_{2\alpha}$
16-ethyl-16-fluoro-2a-homo-20-nor-PGF 2α
16,16-difluoro-2a,2b-dihomo-PGF$_{2'\alpha}$
16-fluoro-16-methyl-2-nor-PGF 2α
16,17-diethyl-16-fluoro-2a-homo-PGF$_{2\alpha}$
18-ethyl-16-fluoro-2a,2b-dihomo-PGF$_{2\alpha}$
16-fluoro- 20-methyl-2-nor-PGF$_{2\alpha}$
16-fluoro-20,20-dimethyl-2a-homo-PGF$_{2\alpha}$
16,16-difluoro-17,20-dimethyl-2a,2b-dihomo-PGF$_{2\alpha}$
16-fluoro- 20-ethyl-2-nor-PGF$_{2\alpha}$
16,16-difluoro- 20-propyl-2a-homo-PGF$_{2\alpha}$
16-fluoro-17,20-dipropyl-2a,2b-dihomo-PGF$_{2\alpha}$
and their racemic mixtures, for example dl-16-fluoro-2,1920-trinor-PGF$_{2\alpha}$. From the 3β-hydroxy XXXIII compounds are obtained the corresponding 15β epimers first as the bis(tetrahydropyranyl) ethers and then as the PGF$_{2\alpha}$ type products and their racemic mixtures, for example:

16-fluoro-2-nor-15β-PGF$_{2\alpha}$
16,16-difluoro-2a-homo-19,20-dinor-15β-PGF$_{2\alpha}$ and dl-16-fluoro-16-methyl-2a,2b-dihomo-19,20-dinor-15β-PGF$_{2\alpha}$.

EXAMPLE 9

16-Fluoro-PGE$_2$, 11,15-Bis(tetrahydropyranyl) Ether (Formula XXXVI: g is 3, M' is

Q is

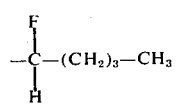

and R$_{10}$ is tetrahydropyranyl.

Refer to Chart C. A solution of the formula-XXXIV bis(tetrahydropyranyl) ether (Example 4, 0.45 g.) in 10 ml. of acetone is cooled to about 0° C. and to it is added dropwise Jones reagent (2.1 g. of chromic anhydride, 6 ml. of water, and 1.7 ml. of concentrated sulfuric acid) until an excess of the reagent persists for 3 min. A few drops of 2-propanol are added and the mixture is concentrated under reduced pressure. The residue is partitioned between dichloromethane and water. The organic phase is dried and concentrated to yield the title compound, free of starting material by TLC.

EXAMPLE 10

16-Fluoro-PGE$_2$ (Formula XIII: C$_n$H$_{2n}$ is —(CH$_2$)$_3$—, g is 3, M''' is

and R$_1$ and R$_2$ are hydrogen).

Refer to Chart C. A solution of the formula-XXXVI bis(tetrahydropyranyl) ether (Example 9, 0.1 g.) in 1.5 ml. of acetonitrile is mixed with 15 ml. of 66% acetic acid. The mixture is heated at 45°–48° C. for 2 hr. and the concentrated under reduced pressure. The residue is taken up in toluene and again concentrated. The residue is chromatographed on silica gel, eluting with the upper layer of a mixture of ethyl acetate-acetic acid-Skellysolve B (isomeric hexanes)-water (90:20:50:100). Those fractions shown by TLC to contain the product free of starting material and impurities are combined and concentrated to yield the title compound, 0.02 g.; mass spectral peaks at 571, 66, 497, and 481.

Following the procedures of Examples 9 and 10, each of the bis(tetrahydropyranyl) ethers described following Examples 4 and 5, and in the following Examples 6, 7, and 8, is transformed to the corresponding 16- (or 16,16-di- ) fluoro-PGE$_2$ type compound or its racemic mixture, for example 16-fluoro-19,20-dinor-PGE$_2$ and dl-16-fluoro-19,20-dinor-PGE$_2$. From the 15β-epimers are obtained the corresponding 15β-PGE$_2$ type epimers, for example 16-fluoro-19,20-dinor-15β-PGE$_2$ and dl-16-fluoro-19,20-dinor-15β-PGE$_2$. As in Example 9, there is first obtained the bis(tetrahydropyranyl) ether of the PGE$_2$ type compound in each instance.

EXAMPLE 11

16-Fluoro-PGF$_{2\beta}$ (Formula XV: C$_n$H$_{2n}$ is —(CH$_2$)$_3$—, g is 3, M is

and R$_1$ and R$_2$ are hydrogen).

Refer to Chart H. A solution of sodium borohydride (300 mg.) in 6 ml. of ice-cold methanol is added to a solution of 16-fluoro-PGE$_2$ (Example 10, 650 mg.) in 30 ml. of methanol at −5° C. The mixture is stirred for an additional 5 min., made slightly acidic with acetic acid, and concentrated under reduced pressure. The residue is extracted with dichloromethane and the organic phase is washed with water, dilute aqueous sodium bicarbonate, and brine, then dried over sodium sulfate and concentrated under reduced pressure. This residue is chromatographed over silica gel wet-packed in ethyl acetate, eluting with 2%, 4%, 7.5%, and 10% ethanol in ethyl acetate. Those fractions containing the title compound free of starting material and impurities, as shown by TLC, are combined and concentrated to yield the formula-XV title compound.

Following the procedure of Example 11, each of the 16- (or 16,16-dl-) fluoro-PGE$_2$ type compounds, their 15$\beta$ epimers, and racemates described following Example 10 is transformed to the corresponding 16- (or 16,16-dl-) fluoro-PGF$_{2\beta}$ type compound or 15$\beta$ epimer or racemic mixture.

EXAMPLE 12

16-Fluoro-PGA$_2$ (Formula XVI: $C_nH_{2n}$ is —$(CH_2)_3$—, $g$ is 3, M''' is

, and R$_1$ and R$_2$ are hydrogen).

Refer to Chart H. A solution of 16-fluoro-PGE$_2$ (Example 10, 300 mg.,) 4 ml. of tetrahydrofuran and 4 ml. of 0.5 N. hydrochloric acid is left standing at 25° C. for 5 days. Brine and dichloromethane-ether (1:3) are added and the mixture is stirred. The organic phase is separated, dried, and concentrated. The residue is dissolved in ether and the solution is extracted with saturated aqueous sodium bicarbonate. The aqueous phase is acidified with dilute hydrochloric acid and then extracted with dichloromethane. This extract is dried and concentrated to yield the formula-XVI title compound.

Following the procedure of Example 12, each of the 16-(or 16,16-di-) fluoro-PGE$_2$ type compounds, 15$\beta$ epimers, and racemates, described following Example 10 is transformed to the corresponding 16- (or 16,16-di-) fluoro-PGA$_2$ type compound or 15$\beta$ epimer or racemic mixture.

EXAMPLE 13

16-Fluoro-PGB$_2$ (Formula XVII: $C_nH_{2n}$ is —$(CH_2)_3$—, $g$ is 3, M''' is

, and R$_1$ and R$_2$ are hydrogen).

Refer to Chart H. A solution of 16-fluoro-PGE$_2$ (Example 10, 200 mg.) in 100 ml. of 50% aqueous ethanol containing about one gram of potassium hydroxide is kept at 25° C. for 10 hr. under nitrogen. The solution is then cooled to 10° C. and neutralized by addition of 3N. hydrochloric acid at 10° C. The resulting solution is extracted repeatedly with ethyl acetate, and the combined ethyl acetate extracts are washed with water and then with brine, dried, and concentrated to yield the formula-XVII title compound.

Following the procedure of Example 13, each of the 16- (or 16,16-di-) fluoro-PGE$_2$ type compounds, their 15$\beta$ epimers, and racemates, described following Example 10 is transformed to the corresponding 16- (or 16,16-di-) fluoro-PGB$_2$ type compound or 15$\beta$ epimer or racemic mixture.

EXAMPLE 14

16-Fluoro-PGE$_1$ (Formula VIII: $C_nH_{2n}$ is —$(CH_2)_3$—, $g$ is 3, M''' is

, and R$_1$ and R$_2$ are hydrogen); and 16-Fluoro-13,14-dihydro-PGE$_1$ (Formula XVIII: $C_nH_{2n}$ is —$(CH_2)_3$—, $g$ is 3, M''' is

, and R$_1$ and R$_2$ are hydrogen).

A mixture of the formula-XXXVI bis(tetrahydropyranyl) ether of 16-fluoro-PGE$_2$ (Example 9, 220 mg.), 5% rhodium-on-alumina catalyst (40 mg.), and 16 ml. of ethyl acetate is stirred under one atmosphere of hydrogen at about 0° C. until substantially all of the starting material has been used, as shown by TLC. The mixture is filtered to remove catalysts, and the filtrate is concentrated. The residue is dissolved in 1 ml. of tetrahydrofuran and 6 ml. of 66% acetic acid and the mixture is warmed to 50° C. for 2.5 hr. The mixture is concentrated under reduced pressure and the residue is chromatographed over silica gel, eluting with the upper layer of a mixture of ethyl acetate-acetic acid- Skellysolve B (isomeric hexanes)-water (90:20:50:100). Those fractions shown by TLC to contain the title compounds free of starting material and impurities are combined and concentrated to yield the title compounds.

Following the procedure of Example 14, each of the PGE$_2$ type bis(tetrahydropyranyl) ethers described following Example 10 is transformed to the corresponding 16- (or 16,-16-di-) fluoro-PGE$_1$ type or 13,14-dihydro-PGE$_1$ type compound, 15$\beta$ epimer, or racemate.

EXAMPLE 15

16-Fluoro-13,14-dihydro-PGE$_1$

A solution of 16-fluoro-PGE$_2$ (Example 10, 100 mg.) in 10 ml. of ethyl acetate is shaken with hydrogen at about one atmosphere pressure at 25° C. in the presence of a 5% palladium-on-charcoal catalyst (15 mg.). Two equivalents of hydrogen are used, whereupon the hydrogenation is stopped and the catalyst is removed by filtration. The filtrate is concentrated under reduced pressure and the residue is chromatographed on silica gel, eluting with ethyl acetate Skellysolve B, (isomeric hexanes) ranging from 50–100% ethyl acetate. Those fractions shown by TLC to contain the desired product free of starting material and impurities are combined and concentrated to give the title compound.

Following the procedures of Examples 11, 12, and 13, each of the 6- (or 16,16-di-) fluoro-PGE$_1$ type of 13,14-dihydro-PGE$_1$ type compounds, 15$\beta$ epimers or racemates described in and following Example 14 is transformed respectively to the corresponding 16- (or 16,16-di-)fluoro-PGF$_{1\alpha}$, -PGF$_{1\beta}$, -PGA$_1$, or -PGB$_1$ type or 16- (or 16,16-di-) fluoro-13,14-dihydro-PGF$_{1\alpha}$, -PGF$_{1\beta}$, -PGA$_1$, or -PGB$_1$ type compound, 15$\beta$ epimer or racemate.

EXAMPLE 16

16-Fluoro-PGF$_{2\alpha}$ Methyl Ester (Formula XIV: C$_n$H$_{2n}$ is —(CH$_2$)$_3$—, g is 3, M''' is

R$_1$ is methyl, and R$_2$ is hydrogen).

A solution of diazomethane (about 0.5 g.) is 25 ml. of diethyl ether is added to a solution of 16-fluoro-PGF$_{2\alpha}$ (Example 5, 50 mg.) in 25 ml. of a mixture of methanol and diethyl ether (1:1). After the mixture has stood at about 25° C. for 5 min., it is concentrated under reduced pressure to yield the title compound.

Following the procedure of Example 16, each of the other 16-fluoro and 16,16-difluoro PGF-type, PGE-type, PGA-type, and PGB-type free acids including their 15β-epimers or racemates defined above is converted to the corresponding methyl ester.

Likewise following the procedure of Example 16, but replacing diazomethane with diazoethane, diazobutane, 1-diazo-2-ethylhexane, and diazodecane, there are obtained the corresponding ethyl, butyl, γ-ethylhexyl, and decyl esters of 16-fluoro-PGF$_{2\alpha}$. In the same manner, each of the other 16-fluoro and 16,16-difluoro PGF-type, PGE-type, PGA-type, and PGB-type free acids including their 15β-epimers or racemates defined above is converted to the corresponding ethyl, butyl, 2-ethylhexyl, and decyl esters.

EXAMPLE 17

16-Fluoro-PGF$_{2\alpha}$ Sodium Salt

A solution of 16-fluoro-PGF$_{2\alpha}$ (Example 5, 100 mg.) in 50 ml. of a water-ethanol mixture (1:1) is cooled to 5° C. and neutralized with an equivalent amount of 0.1 N. aqueous sodium hydroxide solution. The neutral solution is concentrated to a residue of the title compound.

Following the procedure of Example 17 but using potassium hydroxide, calcium hydroxide, tetramethylammonium hydroxide, and benzyltrimethylammonium hydroxide in place of sodium hydroxide, there are obtained the corresponding salts of 16-fluoro-PGF$_{2\alpha}$.

Likewise following the procedure of Example 17 each of the 16-fluoro- and 16,16-difluoro PGE-type, PGF-type, PGA-type, and PGB-type acids including their 15β-epimers or racemates defined above is transformed to the sodium, potassium, calcium, tetramethylammonium, and benzyltrimethylammonium salts.

EXAMPLE 18

16,16-Difluoro-PGF$_{2\alpha}$ Methyl Ester (Formula XIV: C$_n$H$_{2n}$ is —(C$_2$)$_3$—, g is 3, M''' is

R$_1$ is methyl, and R$_2$ is fluoro)

Refer to Chart B. a. There is first prepared dimethyl 2-oxo-3,3-difluoroheptylphosphonate. Following the procedure of Example 1-a, methyl 2,2-difluorohexanoate (prepared from methyl 2-oxohexanoate by reaction with MoF$_6$.BF$_3$,b.p. 61°–66° C./mm.) is reacted with dimethyl methylphosphonate to yield the desired product, b.p. 93°–6° C./0.4 mm., and having mass spectral peaks at 258, 238, 202, 151, 109, and 79.

b. The formula-XXVIII aldehyde (Preparation 1, m.p. 115°–117°C.) is reacted with the above phosphonate following the procedure of Example 1-b to yield the corresponding formula-XXIX difluoro intermediate, m.p. 70°–72°C.

c. Following the procedure of Example 2, the formula-XXIX 3-oxo- 4,4-difluoro compound above is reduced to the corresponding formula-XXX 3-hydroxy- 4,4-difluoro compounds which are separated by silica gel chromatography. The 3α-hydroxy isomer has R$_f$ 0.50 (TLC on silica gel plate in ethyl acetate-Skellysolve B (1:1); the 3β-hydroxy isomer has R$_f$ 0.43.

d. Following the procedure of Example 3, the benzoyloxy group of the 3α-hydroxy formula-XXX compound is replaced by hydrogen to form the corresponding formula-XXXI compound (R$_f$ 0.37 in ethyl acetate-Skellysolve B (2:1)) which is transformed to the formula-XXXII 4,4-difluoro intermediate (R$_f$ 0.6 in ethyl acetate-Skellysolve B (1:1)) and thence to the formula-XXXIII difluoro lactol.

e. Following the procedure of Example 4, and using the formula-XXXIII difluoro lactol above instead of the formula-XXXIII monofluoro lactol of that Example, there is obtained 16,16-difluoro-PGF$_{2\alpha}$, having mass spectral peaks at 678, 663, 644, 588, 571, 472, and 363 (trimethylsilyl derivative).

f. Finally, following the procedure of Example 16, there is obtained the title compound, having mass spectral peaks at 605, 600, 589, 585, 530, 513, 510, 440, 423, and 217 (trimethylsilyl derivative).

EXAMPLE 19

3α-Benzoyloxy-5α-hydroxy-2β-(3α-methoxy-4,4-difluoro-trans-1-octenyl)-1α-cyclopentaneactic Acid γ-lactone (Formula

Q is

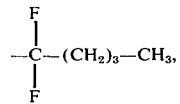

and R$_3$ is benzoyl).

Refer to Chart D. A mixture of the formula-XXX alpha hydroxy compound (Example 18, 2.0 g.), silver oxide (4.0 g.), and 50 ml. of methyl iodide is stirred and heated at reflux for 68 hr. The mixture is cooled and filtered, and the filtrate concentrated. The residue is subjected to silica gel chromatography to obtain the formula-XXXIX title compound.

Following the procedure of Example 19, but replacing the methyl iodide of that example with other alkyl halides, there are obtained the corresponding formula-XXXIX alkyl esters. Thus, with methyl bromide, ethyl chloride, isopropyl iodide, butyl bromide, or pentyl iodide, there are obtained the formula-XXXIX compound in which R$_{18}$ is methyl, ethyl, isopropyl, n-butyl or n-pentyl.

EXAMPLE 20

15d-16,16-d-fluoro-PGE$_{2\alpha}$ Methyl Ester, 15-Methyl Ether (Formula XIV: C$_n$H$_{2n}$ is —(CH$_2$)$_3$—, g is 3, M''' is

R$_1$ is methyl, and R$_2$ is fluoro).

Refer to Chart D. Following the procedures of Example 18 but replacing the formula-XXX compound in step d with the 3α-methoxy formula-XXX compound of Example 19, there are obtained the corresponding intermediates and products as follows:

3α,5α-dihydroxy-2β-(3α-methoxy-4,4-difluoro-trans-1-octenyl)-1α-cyclopentaneacetic acid γ-lactone and its tetrahydropyranyl ether;

3α,5α-dihydroxy- 2β-(3α-methoxy- 4,4-difluoro-trans-1-octenyl)-1α-cyclopentaneacetaldehyde γ-lactol, tetrahydropyranyl ether (formula XL);

16,16-difluoro-PGF$_{2\alpha}$, 11-tetrahydropranyl ether, 15-methyl ether; 16,16-difluoro-PGF$_{2\alpha}$, 15-methyl ester (formula XLI); and the title compound.

EXAMPLE 21

15a-15-methyl-16,16-difluoro-PGF$_{2\alpha}$ , methyl Ester (Formula XIV: C$_n$H$_{2n}$ is —(CH$_2$)$_3$—, g is 3, M''' is

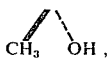

R$_1$ is methyl, and R$_2$ is fluoro).

Refer to Chart E. A solution of the formula-XXIX oxo compound wherein C$_n$H$_{2n}$ is trimethylene, R$_2$ is fluoro, and R$_3$ is benzoyl (Example 18b, 0.2 g.) in 15 ml. of tetrahydrofuran is treated, with stirring a —78° C., with 3M methyl magnesium bromide in ether, added dropwise. After 2 hr. there is added dropwise to the mixture at —78° C. 10 ml. of saturated aqueous ammonium chloride. The mixture is warmed to 25° C. and diluted with diethyl ether and water. The organic phase is washed with brine, dried and concentrated to the mixed 3α and 362 formula-XLII compounds, which are separated by silica gel chromatography to yield 3α-benzoyloxy-5α-hydroxy- b 2β-(3α-hydroxy-3-methyl-4,4-difluoro-trans-1-octenyl)-1α-cyclopentaneacetic acid γ-lactone (formula XLII).

Employing the procedures of Examples 18d–f but replacing the formula-XXX compound with the 3α formula-XLII compound above, there are obtained the corresponding intermediates and products as follows:

3α,5α-dihydroxy-2β-(3α-hydroxy- b 3-methyl-4,4-difluoro-trans-1-ocetnyl)-1α-cyclpentaneacetic acid γ-lactone (formula XLIII) and its bis-(tetrahydropyranyl ether) (formula XLIV);

3α,5α-dihydroxy-2β-(3α-hydroxy-3-methyl-4,4-difluoro-trans-1-octenyl)-1α-cyclopentaneacetaldehyde γ-lactol, bis(tetrahydropyranyl ether) (formula XLV);

15a-15-methyl-16,16-difluoro-PGF$_{2\alpha}$ , 11,15 bis(tetrahydropyranyl ether);

15d-15-methyl-16,16-difluoro-PGF$_{2\alpha}$ , and title compound.

I claim;

1. An optically active compound of the formula

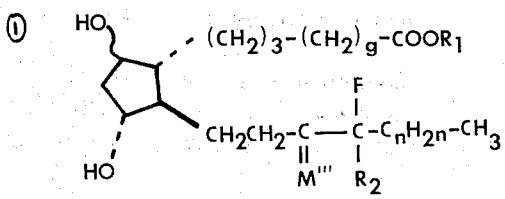

or a racemic compound of that formula and the mirror image thereof, wherein ~ indicates attachment of hydroxyl to the ring in alpha or beta configuration; wherein g is an integer from 2 to 5, inclusive, wherein C$_n$H$_{2n}$ is alkylene of one to 9 carbon atoms, inclusive, with one to 6 carbon atoms, inclusive, in the chain between —CFR$_2$— and terminal methyl; wherein M''' is

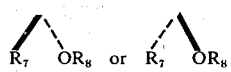

wherein R$_7$ and R$_8$ are hydrogen or alkyl of one to 4 carbon atoms, inclusive, being the same or different; wherein R$_1$ is hydrogen or alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; and wherein R$_2$ is hydrogen, methyl, ethyl, or fluoro; including the lower alkanoates thereof, and the pharmacologically acceptable salts thereof when R$_1$ is hydrogen.

2. A compound according to claim 1 wherein ~ is alpha.

3. A compound according to claim 2 wherein M''' is

4. A compound according to claim 2 wherein R$_7$ and R$_8$ are either hydrogen or methyl, being the same or different, and at least one of R$_7$ and R$_8$ is methyl.

5. A compound according to claim 3 wherein R$_7$ and R$_8$ are hydrogen.

6. A compound according to claim 5 wherein g is 3.

7. A compound according to claim 6 wherein C$_n$H$_{2n}$ has 3 carbon atoms in the chain between —CFR$_2$— and terminal methyl.

8. A compound according to claim 7 wherein R$_2$ is hydrogen.

9. A compound according to claim 8 wherein R$_1$ is alkyl of one to 12 carbon atoms, inclusive.

10. A compound according to claim 8 wherein R$_1$ is hydrogen.

11. 16-Fluoro-13,14-dihydro-PGF$_{1\alpha}$ , optically active compounds according to claim 10.

12. A compound according to claim 7 wherein R$_2$ is fluoro.

13. A compound according to claim 12 wherein R$_1$ is alkyl of one to 12 carbon atoms, inclusive.

14. 16,16-Difluoro-13,14-dihydro-PGF$_{1\alpha}$ , methyl ester, an optically active compound according to claim 13 wherein R$_1$ is methyl.

15. A compound according to claim 6 wherein C$_n$H$_{2n}$ has one, 2, 4, 5, or 6 carbon atoms in the chain between —CFR$_2$— and terminal methyl.

16. A compound according to claim 5 wherein g is 2, 4, or 5.
17. 2a,2b-Dihomo-16,16-difluoro-13,14-dihydro-PGF$_{1\alpha}$, a compound according to claim 16.
18. A compound according to claim 2 wherein M''' is 
19. A compound according to claim 1 wherein ~ is beta.
* * * * *